(12) United States Patent
Netzel et al.

(10) Patent No.: US 8,301,238 B2
(45) Date of Patent: Oct. 30, 2012

(54) TWO-PART ELECTROTRANSPORT DEVICE

(75) Inventors: Zita S. Netzel, Los Altos, CA (US); John Lemke, Pleasanton, CA (US); David Seward, Seattle, WA (US); Brian W. Read, Brier, WA (US); Bradley E. White, Mason, OH (US); Corinna X. Chen, Oakland, CA (US); Paul Hayter, Mountain View, CA (US)

(73) Assignees: Incline Therapeutics, Inc., Redwood City, CA (US); Alza Corporation, Vacaville, CA (US)

(*) Notice: Subject to any disclaimer, the term of this patent is extended or adjusted under 35 U.S.C. 154(b) by 0 days.

(21) Appl. No.: 13/250,031

(22) Filed: Sep. 30, 2011

(65) Prior Publication Data

US 2012/0253263 A1    Oct. 4, 2012

Related U.S. Application Data

(60) Provisional application No. 61/470,352, filed on Mar. 31, 2011.

(51) Int. Cl.
*A61N 1/30* (2006.01)
(52) U.S. Cl. .......................................... 604/20
(58) Field of Classification Search .................... 604/20, 604/891.1, 892.1
See application file for complete search history.

(56) References Cited

U.S. PATENT DOCUMENTS

| | | | |
|---|---|---|---|
| 4,731,926 A | 3/1988 | Sibalis | |
| 5,057,072 A | 10/1991 | Phipps | |
| 5,084,008 A | 1/1992 | Phipps | |
| 5,135,479 A * | 8/1992 | Sibalis et al. | 604/20 |
| 5,147,297 A | 9/1992 | Myers et al. | |
| 5,199,155 A | 4/1993 | Cord et al. | |
| 5,224,927 A * | 7/1993 | Tapper | 604/20 |
| H1324 H | 6/1994 | Dalke et al. | |
| 5,320,597 A | 6/1994 | Sage, Jr. et al. | |
| 5,358,483 A | 10/1994 | Sibalis | |
| D352,357 S | 11/1994 | Ashley | |
| 5,445,609 A | 8/1995 | Lattin et al. | |
| 5,458,569 A | 10/1995 | Kirk, III et al. | |
| D372,098 S | 7/1996 | Lattin et al. | |
| 5,551,953 A * | 9/1996 | Lattin et al. | 604/20 |
| 5,562,607 A * | 10/1996 | Gyory | 604/20 |
| 5,603,693 A | 2/1997 | Frenkel et al. | |
| D384,745 S | 10/1997 | Lattin et al. | |

(Continued)

FOREIGN PATENT DOCUMENTS

EP    1532995    5/2005

(Continued)

*Primary Examiner* — Kevin C Sirmons
*Assistant Examiner* — Michael J Anderson
(74) *Attorney, Agent, or Firm* — Shay Glenn LLP

(57) ABSTRACT

A switch operated therapeutic agent delivery device is described. The device comprises two parts, which are assembled by a user prior to use. A first part contains a power supply and circuitry for the device; and a second part comprises electrodes and reservoirs containing the therapeutic agent to be delivered. The action of combining the two parts of the device causes the two parts to be irreversibly coupled together, completes an electrical connection between the two parts, and closes one or more switches, thereby connecting a power source, such as a battery, into the device's circuitry, thereby powering the device on so that it is ready for use. The device can then be attached to a patient, who can operate the device by pressing a button in a proper sequence.

29 Claims, 10 Drawing Sheets

U.S. PATENT DOCUMENTS

| | | | |
|---|---|---|---|
| 5,718,562 A | 2/1998 | Lawless et al. | |
| 5,879,143 A | 3/1999 | Cote et al. | |
| 5,919,155 A | 7/1999 | Lattin et al. | |
| 5,928,196 A | 7/1999 | Johnson et al. | |
| 6,039,977 A | 3/2000 | Venkatraman et al. | |
| 6,049,733 A | 4/2000 | Phipps et al. | |
| 6,086,572 A * | 7/2000 | Johnson et al. | 604/503 |
| 6,167,302 A * | 12/2000 | Millot | 604/20 |
| 6,171,294 B1 | 1/2001 | Southam et al. | |
| 6,181,963 B1 | 1/2001 | Chin et al. | |
| 6,216,033 B1 | 4/2001 | Southam et al. | |
| 6,355,025 B1 * | 3/2002 | Phipps et al. | 604/501 |
| 6,453,195 B1 | 9/2002 | Thompson | |
| 6,949,081 B1 * | 9/2005 | Chance | 604/67 |
| 7,016,724 B2 * | 3/2006 | Henley et al. | 604/20 |
| 7,660,627 B2 | 2/2010 | McNichols et al. | |
| 7,844,326 B2 | 11/2010 | Dent et al. | |
| 2002/0128591 A1 | 9/2002 | Kleiner et al. | |
| 2002/0183702 A1 | 12/2002 | Henley et al. | |
| 2002/0198504 A1 | 12/2002 | Risk et al. | |
| 2003/0191946 A1 | 10/2003 | Auer et al. | |
| 2005/0004506 A1 * | 1/2005 | Gyory | 604/20 |
| 2008/0234627 A1 | 9/2008 | Dent et al. | |
| 2008/0234628 A1 * | 9/2008 | Dent et al. | 604/20 |

FOREIGN PATENT DOCUMENTS

| | | |
|---|---|---|
| GB | 2239803 | 7/1991 |
| WO | WO 96/36394 A1 | 11/1996 |
| WO | WO 01/41863 A1 | 6/2001 |
| WO | WO 2006/077262 A1 | 7/2006 |

* cited by examiner

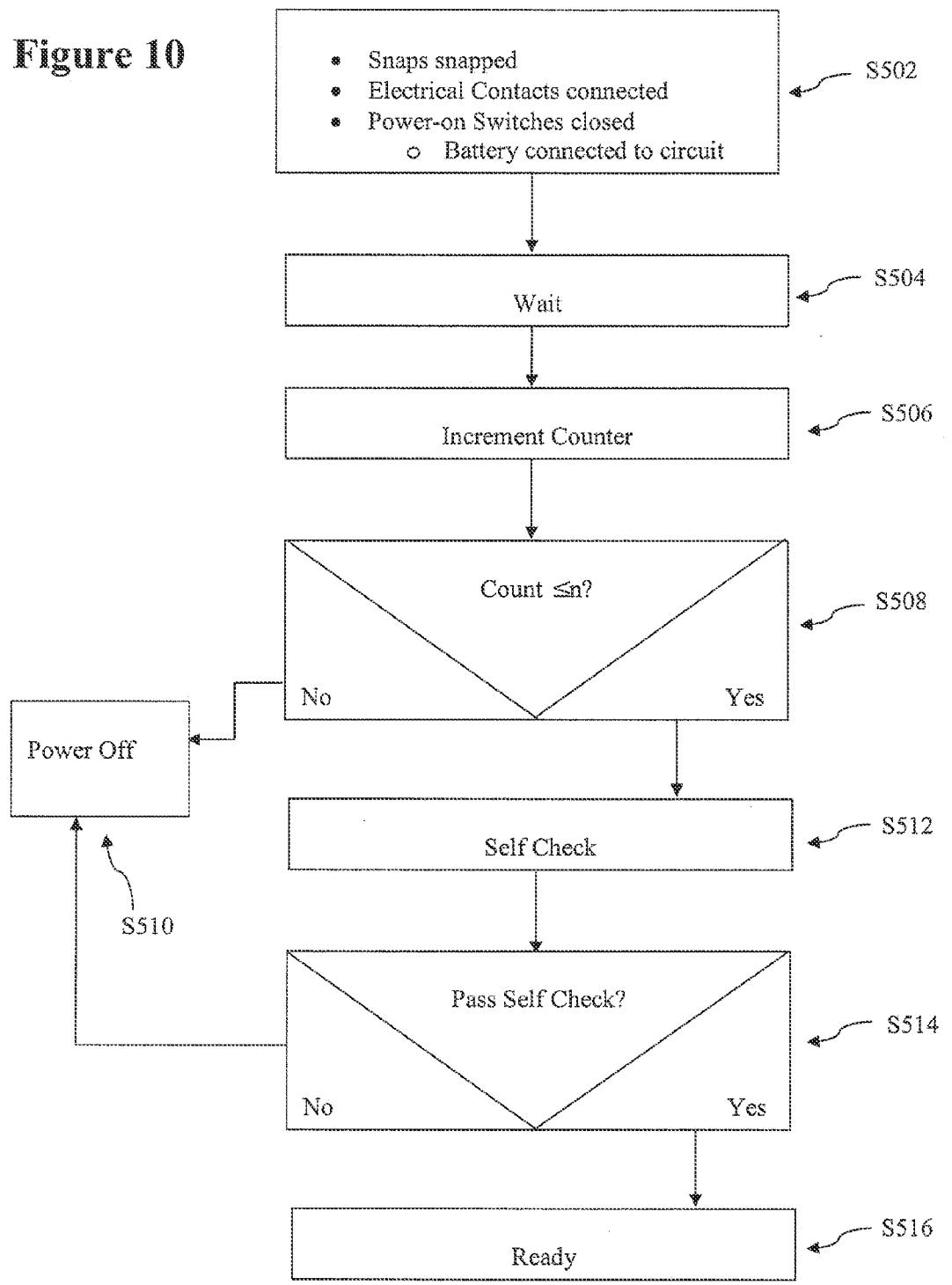

TWO-PART ELECTROTRANSPORT DEVICE

CROSS REFERENCE TO RELATED APPLICATION

This application claims the benefit under 35 U.S.C. 119 of U.S. Provisional Patent Application No. 61/470,352, filed Mar. 31, 2011, titled "Two-Part Electrotransport Device". This application is herein incorporated by reference in its entirety.

BACKGROUND

The delivery of active pharmaceutical agents through the skin provides many advantages, including comfort, convenience, and non-invasiveness. This technology may also avoid gastrointestinal irritation and the variable rates of absorption and metabolism, including first pass effects, encountered in oral delivery. Transdermal delivery can also provide a high degree of control over blood concentrations of any particular active agent.

One method for transdermal delivery of such active agents involves the use of electrical current to actively transport the active agent into the body through intact skin by electrotransport. Electrotransport techniques may include iontophoresis, electroosmosis, and electroporation. Electrotransport devices, such as iontophoretic devices are known in the art. See, e.g., U.S. Pat. No. 6,216,033 B1 (Southam, et al.) One electrode, which may be referred to as the active or donor electrode, is the electrode from which the active agent is delivered into the body. The other electrode, which may be referred to as the counter or return electrode, serves to close the electrical circuit through the body. In conjunction with the patient's body tissue, e.g., skin, the circuit is completed by connection of the electrodes to a source of electrical energy, and usually to circuitry capable of controlling the current passing through the device. If the substance to be driven into the body is ionic and is positively charged, then the positive electrode (the anode) will be the active electrode and the negative electrode (the cathode) will serve as the counter electrode. If the ionic substance to be delivered is negatively charged, then the cathodic electrode will be the active electrode and the anodic electrode will be the counter electrode.

A switch operated therapeutic agent delivery device can provide single or multiple doses of a therapeutic agent to a patient by activating a switch. Upon activation, such a device delivers a therapeutic agent to a patient. A patient-controlled device offers the patient the ability to self-administer a therapeutic agent as the need arises. For example, the therapeutic agent can be an analgesic agent that a patient can administer whenever sufficient pain is felt.

There have been suggestions to provide different parts of an electrotransport system separately and connect them together for use. For example, it has been suggested that such connected-together systems might provide advantages for reusable controller circuit. In reusable systems, the drug-containing units are disconnected from the controller when the drug becomes depleted and a fresh drug-containing unit is then connected to the controller again. Examples of electrotransport devices having parts being connected together before use include those described in U.S. Pat. No. 5,320,597 (Sage, Jr. et al); U.S. Pat. No. 4,731,926 (Sibalis), U.S. Pat. No. 5,358,483 (Sibalis), U.S. Pat. No. 5,135,479 (Sibalis et al.), UK Patent Publication GB2239803 (Devane et al), U.S. Pat. No. 5,919,155 (Lattin et al.), U.S. Pat. No. 5,445,609 (Lattin et al.), U.S. Pat. No. 5,603,693 (Frenkel et al.), WO1996036394 (Lattin et al.), and US 2008/0234628 A1 (Dent et al.).

There remain issues to be resolved and problems to be overcome in the art of electrotransport of therapeutic agents.

SUMMARY OF THE DISCLOSURE

The present disclosure describes a two-part electrotransport therapeutic agent delivery device, such as an iontophoresis device, in which the two parts of the device are provided separately and assembled to form a unitary, powered-on device at the point of use—e.g. just prior to use. One part of the device, which may be referred to herein as the electrical module, holds essentially all of the circuitry, as well as the power source (e.g. battery), for the device; and the other part, which may be referred to herein as the reservoir module, contains the therapeutic agent to be delivered along with electrodes and hydrogels necessary to deliver the therapeutic agent to a patient. The device is configured such that the power source is kept electrically isolated from the rest of the circuitry in the electrical module until the electrical module is combined with the reservoir module. The combination of the modules occurs in a single action by a user, along with connection of the battery into the circuitry. Thus, embodiments provided herein permit the combination of the electrical module and the reservoir module, whereby in a single action the two modules form a single unit and the battery is introduced into the circuitry, thereby powering on the device, in a single action by the user.

The present invention addresses various needs, and provides various advantages, in the art of patient-controlled drug administration devices, especially those devices that are subject to humidity and other contaminants during storage and use, such as iontophoresis devices. Electrical components, especially those that have electrical charges applied to them, are especially vulnerable to corrosion, particularly when they are exposed to humidity and/or contaminants, such as ions and particulate contaminants. By keeping the electrical circuitry isolated from the hydrogels in the reservoir module prior to use, the device described herein reduces the tendency of electronic circuitry to be corroded by humidity emitted from the hydrogels. In embodiments of the device described herein, not only is the electrical circuitry maintained in isolation from the water-containing reservoir module prior to use, thereby reducing water contamination of the circuitry, the battery itself is maintained in electronic isolation from the electronic circuitry prior to combination of the two modules. Thus, unlike previously devised electrotransport devices, which generally comprised a battery that was maintained in the electrical circuitry, embodiments of the device provided herein keep the battery out of the circuit until the two modules are combined, which prevents battery drain prior to use and prevents the circuitry from being subjected to electrostatic charges that can accelerate, or even cause, corrosion. In embodiments of the device provided herein, the two modules are combined (e.g. snapped) together and the battery is connected into the circuit in a single action by a user, such as a health care professional. In embodiments described herein, connection of the battery into the circuit turns the device "on" in the same single action. In some embodiments, once the device has been powered on, a controller or similar device runs one or more power-on checks to ensure that the device is in proper operating condition, and at least in some embodiments, signals a user that the device is ready for use. In certain embodiments, the controller or similar device is configured to detect an error state, such as a signal that indicates that the device is corroded, or an indication that the device has been previously used. In some such embodiments, the device then signals the user that an error has been detected (e.g. through a visual display or an audible alarm) and/or powers down. In some such embodiments, e.g. when the device is intended for a single use, once the device is powered down (e.g. by separating the two modules) the device will not again be operative.

In one aspect of the device described herein, the two parts (modules) are combined to form a single unit and the battery is connected into the circuitry, from which it has been previously electrically isolated, in a single action. Thus, there is no need to power the device on through some separate action, such as actuating a separate switch mechanism or removing a tab. Once the two modules are combined to for a single unit, the device is powered on and is enabled to perform the various functions that are required of it, such as running self diagnostics, receiving an activation signal from a user (e.g. a healthcare professional or patient) to effect drug delivery, and optionally powering off (e.g. at the end of its predetermined useful lifetime and/or upon detection of an error or other appropriate signal.)

In one aspect of the device described herein, the device is intended for single use. The device is configured to ensure that the electronic circuitry cannot be re-used, that is, the two modules may not be separated from one another and then rejoined to form an operative device, nor can the electrical module be combined with a different reservoir module to form an operative device. Such configuration includes single use (one way) couplers (e.g. single use snaps), electronic logic that detects and prevents an attempt to use the circuitry more than once (e.g. hardware, software, firmware, memory, etc., or a combination of two or more thereof), or various combinations thereof. In some embodiments, the device includes both mechanical and electrical means to prevent re-use.

In some embodiments, the device also includes one or more keying features designed to assist the user in combining the modules in a single configuration, which is the only operative configuration. Such keying features may include different sized couplers, variously shaped complementary external features of the modules, and visual alignment cues, or combinations of two or more thereof, which ensure that the user combines the two modules in the single, operative configuration only.

Some embodiments described herein provide an electrotransport drug delivery device comprising an electrical module and a reservoir module, the electrical module and the reservoir module being configured to be combined to form a unitary, activated drug delivery device prior to use, wherein: (a) the electrical module comprises: (i) circuitry; (ii) electrical outputs for connecting the circuitry to input connectors on the reservoir module when the electrical module is combined with the reservoir module; (iii) one or more power-on contacts between the circuitry and the battery; and (iv) a battery, which is isolated from the circuitry by the one or more power-on contacts while at least one of the power-on contacts remains open, and which is connected into the circuitry when each of the one or more power-on contacts is closed by one or more battery contact actuators on the reservoir module when the electrical module and the reservoir module are combined; and (b) the reservoir module comprises: (i) electrical inputs for electrically connecting the circuitry in the electrical module to at least a pair of active electrodes in the reservoir module when the electrical module is combined with the reservoir module; and (ii) one or more battery contact actuators, each of which is configured to close a corresponding power-on contact when the electrical module is combined with the drug reservoir, such that when each of the power-on contacts is closed by a power-on actuator, the battery is connected into the circuitry and the device is powered on. In some embodiments, at least one seal is formed upon combining the electrical module and the reservoir module. In some embodiments, at least one seal is maintained at each power-on contact before, during, and/or after the electrical module is combined with the reservoir module. In some embodiments, at least one seal is a flexible polymer cover over the power-on contact, which is configured to be deformed by an actuator when the electrical module is combined with the reservoir module, whereby the actuator mechanically acts through the seal to close the power-on contact. In some embodiments, at least one seal is maintained at each electrical output before, during, and after the electrical module is combined with the reservoir module. In some embodiments, at least one seal is water- or particulate-tight. In some embodiments, at least one seal is water-tight and particulate-tight. In some embodiments, the electrical outputs are configured to flex while continuously applying a force on the electrical inputs of the reservoir module to ensure good electrical connection between the two. In some embodiments, at least one surface of the electrical inputs is substantially planar. In some embodiments, the electrical module and the reservoir module are separately manufactured, packaged and/or shipped. In some embodiments, the electrical module and the reservoir module are configured to be combined to form a powered on drug delivery device just prior to attachment to a patient. In some embodiments, the device comprises one or more couplers on the reservoir module or the electrical module, each of which couples with a corresponding coupler receptor on the electrical module or reservoir module, respectively, to prevent the unitary drug delivery device from being easily separated. In some embodiments, each coupler is a snap, which is mechanically biased to snap into a corresponding snap receptor. In some embodiments, each snap is a one-way snap. In some embodiments, the device comprises two or more couplers and two or more corresponding coupler receptors. In some embodiments, at least two of the two or more couplers and two or more corresponding coupler receivers are of different sizes, whereby a first coupler can be inserted only into a first coupler receiver, thereby ensuring that the device can be assembled in only one configuration. In some embodiments, each coupler is biased so that once each coupler is engaged with its corresponding receptor, the device cannot be disassembled without breaking or deforming at least one of the couplers so that it is no longer operable. In some embodiments, the power-on contact is configured to be actuated by the battery contact actuator, thereby connecting the battery to the circuit, simultaneously, or substantially simultaneously, with coupling of the coupler and the coupler receptor. In some embodiments, one or more of the couplers and/or coupler receptors are water- and/or particulate-tight. In some embodiments, at least one water- and/or particulate-tight seal is formed between at least one coupler and at least one coupler receptor when they are coupled. In some embodiments, the battery contact actuator is a member, such as a post, that protrudes from the reservoir module and depresses a receptacle on the electrical module, the receptacle being in mechanical communication with the power-on contact such that the battery is connected into the circuit when the battery contact actuator depresses the receptacle. In some embodiments, the battery contact actuator is a post and the receptacle is a deformable member. In some embodiments, the deformable member is indented, flush or domed. In some embodiments, the device includes at least two power-on contacts and at least two corresponding battery contact actuators. In some embodiments, the battery is housed in a compartment that protrudes from the electrical module, which compartment has an outer shape that is configured to a corresponding indentation in the reservoir module such that the battery compartment fits snugly within the indentation in only one configuration when the electrical module and the reservoir module are combined to form the unitary device. In some embodiments, the electrical inputs on the reservoir module are flat or substantially flat electrically conductive metal, such as copper, brass, nickel, stainless steel, gold, silver or a combination thereof. In some embodiments, one or more of the electrical outputs includes one or more bumps protruding from electrical outputs. In some embodiments, the bumps are on one or more hats (described herein) protruding from the electrical module. In some embodiments, the hats are biased to maintain positive contact between the electrical outputs on the electrical module and the electrical inputs on the reservoir module. In some embodiments, the bias is provided by one or more springs or elastic members. In some embodiments, the bias is provided by one or more coil springs, beam springs or elastic members. In some embodiments, the device comprises one or more sealing members for providing a seal around the electrical inputs and outputs when the electrical module and the reservoir module are combined to form the unitary device. In some embodiments, the seal is a ring seal. In some embodiments, the seal is water- and/or particulate-tight. In some embodiments, the reservoir module is sealed in a container configured to be removed prior to combining the electrical module with the reservoir module to form the unitary device. In some embodiments, the container is a water- and/or particulate-tight pouch. In some embodiments, the electrical module further comprises a controller. In some embodiments, the controller is configured to execute a power-on check when the battery is connected into the circuitry. In some embodiments, the power-on check includes a battery test, an ASIC test, a power source test, an LCD check. In some embodiments, the device is configured to increment a logic flag when the electrical module is combined with the reservoir module, and wherein the device is configured such that, if the logic flag has met or exceeded a predetermined value, the device will either not power on or will power off if it has already powered on. In some embodiments, the device is configured to record an error code if the logic flag has met or exceeded a predetermined value. In some embodiments, the circuitry comprises a printed circuit board. In some embodiments, the one or more power-on contacts are configured to remove the battery from the circuitry if the electrical module and the reservoir module are separated after they have been combined. In some embodiments, the electrical module is configured to flex while maintaining a seal. In some embodiments, the seal is water- and/or particulate-tight. In some embodiments, the device further comprises an activation switch. In some embodiments, the device further comprises a liquid crystal diode (LCD) display, a light emitting diode (LED) display, an audio transducer, or a combination of two or more thereof.

Some embodiments described herein provide a method of drug delivery comprising: (a) combining an electrical module and a reservoir module to form a unitary powered-on drug delivery device, wherein: (i) the electrical module comprises: (1) circuitry; (2) electrical outputs for connecting the circuitry to input connectors on the reservoir module when the electrical module is combined with the reservoir module; (3) at least one power-on contact between the circuitry and the battery; and (4) a battery, which is isolated from the circuitry by the power-on contact until the power-on contact is actuated by a battery contact actuator on the reservoir module, and which is connected into the circuitry when the power-on contact is actuated by the battery contact actuator on the reservoir module when the electrical module and the reservoir module are combined; and (ii) the reservoir module comprises: (1) electrical inputs for electrically connecting the circuitry in the electrical module to at least a pair of active electrodes in the reservoir module when the electrical module is combined with the reservoir module; and (2) at least one battery contact actuator, which is configured to actuate said power-on contact when the controller module is combined with the drug delivery module, thereby connecting the battery into the circuitry; (b) applying the unitary device to a patient; and (c) activating the device to effect delivery of the drug to the patient.

Some embodiments described herein provide a process of manufacturing a drug delivery device, comprising: (a) assembling an electrical module comprising: (i) circuitry; (ii) electrical outputs for connecting the circuitry to input connectors on the reservoir module when the electrical module is combined with the reservoir module; (iii) at least one power-on contact between the circuitry and the battery; and (iv) a battery, which is isolated from the circuitry by the power-on contact until the power-on contact is actuated by a battery contact actuator on the reservoir module, and which is connected into the circuitry when the power-on contact is actuated by the battery contact actuator on the reservoir module when the electrical module and the reservoir module are combined; and (b) assembling a reservoir module comprising: (i) electrical inputs for electrically connecting the circuitry in the electrical module to at least a pair of active electrodes in the reservoir module when the electrical module is combined with the reservoir module; and (ii) at least one battery contact actuator, which is configured to actuate said power-on contact when the controller module is combined with the drug delivery module, thereby connecting the battery into the circuitry; and (c) packaging the electrical module and the reservoir module. In some embodiments, the process comprises sealing the reservoir module in a water- and/or particulate-tight pouch.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which similar features are identified with the same numbers, of which:

FIG. 10 is a flow chart showing a power-on sequence of a device as described herein;

DETAILED DESCRIPTION

Figure 1:
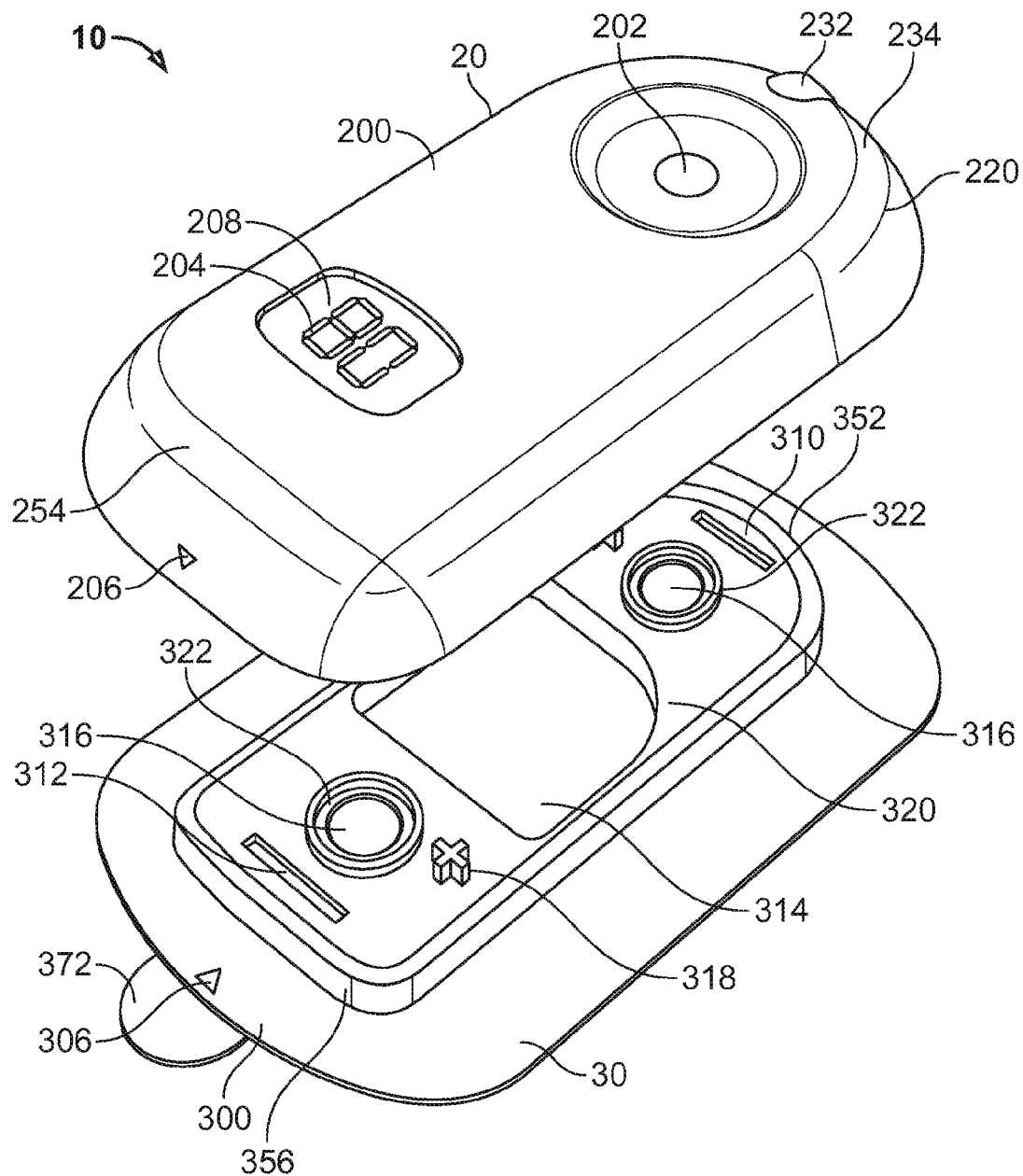
FIG. 1 illustrates an exemplary therapeutic agent delivery system in two parts.

The present disclosure describes a two-part electrotransport therapeutic agent delivery device, such as an iontophoresis device, in which the two parts of the device are provided separately and assembled to form a unitary, powered-on device at the point of use—that is to say just prior to use. One part of the device, which may be referred to herein as the electrical module, holds essentially all of the circuitry, as well as the power source (e.g. battery), for the device; and the other part, which may be referred to herein as the reservoir module, contains the therapeutic agent to be delivered along with electrodes and hydrogels necessary to deliver the therapeutic agent to a patient. The device is configured such that the power source is kept electrically isolated from the rest of the circuitry in the electrical module until the electrical module is combined with the reservoir module. Thus, embodiments provided herein permit the combination of the electrical module and the reservoir module, whereby in a single action the two modules form a single unit and the battery is introduced into the circuitry, thereby powering on the device, in a single action by the user.

Unless otherwise indicated, singular forms "a", "an" and "the" are intended to include plural referents. Thus, for example, reference to "a polymer" includes a single polymer as well as a mixture of two or more different polymers, "a contact" may refer to plural contacts, "a post" may indicate plural posts, etc.

As used herein, the term "user" indicates anyone who uses the device, whether a healthcare professional, a patient, or other individual, with the aim of delivering a therapeutic agent to a patient.

As used herein, the term simultaneous, and grammatical variants thereof, indicates that two or more events occur at about the same time and/or that they occur without any intervening step. For example, when connection of the modules occurs simultaneously with connection of the battery into the circuit, the term "simultaneously" indicates that when the modules are connected, the battery is connected into the circuit at about the same time, in a single action by the user, and that there is no additional step necessary on the part of the user to connect the battery to the circuit. The term "substantially simultaneous" and grammatical variants indicates that two events occur at about the same time and no significant action is required by the user between the two events. For the sake of illustration only, such a significant action could be the activation of a separate switch (other than the herein-described power-on switches), removal of a tab, or other action to connect the battery in the electrical module to the circuitry therein upon connection of the two modules to one another.

Unless otherwise modified herein, the term "to break" and grammatical variants thereof refers to destroying or deforming something to the point that it is no longer operable for its intended purpose.

The present disclosure provides an electrotransport device that is assembled before use for electrotransport delivery of ionic compounds (e.g., ionic drugs such as fentanyl and analogs, polypeptides, and the like) through a surface, such as skin. The electrotransport device comprises a top or upper portion, herein referred to as an electrical module, and a bottom or lower portion, herein referred to as a reservoir module. The electrical module contains circuitry (e.g. a printed circuit board), a power source (e.g. a battery), one or more power-on switches and such other circuitry as may be deemed desirable for operation of the device (such as an activation switch, a controller, a liquid crystal diode (LCD) display, a connector, a light emitting diode (LED), an audible indicator (e.g. a sound transducer), or combinations thereof), as well as electrical output contacts for electrically connecting the electrical module to a reservoir module. When obtained by the user, the electrical module is separated from the reservoir module. In this state, the battery is maintained outside of the electrical circuit (though within the electrical module), thereby preventing the battery from discharging through the circuit prior to use. Because the battery is electrically isolated from the circuit prior to combining the electrical and reservoir modules, the circuitry has essentially no electrical charge applied to it prior to combination of the two modules, rendering the circuitry far less susceptible to corrosion than if the battery were in the circuit.

The reservoir module contains electrodes and reservoirs for delivery of therapeutic agent to a patient. At least one reservoir contains the therapeutic agent to be delivered. At least one counter reservoir is provided, which generally contains no therapeutic agent, though in some embodiments it is possible for the counter reservoir to contain therapeutic agent. Prior to being connected to the electrical module, the reservoir module is maintained both physically and electrically isolated from the electrical module. For example, one or both of the modules may be sealed in a pouch, such as a plastic or foil pouch, in order to prevent contamination with water, particulates, vapors, etc. As a non-limiting example, both the electrical and the reservoir modules may be sealed in the same pouch. As a further non-limiting example, the reservoir module may be sealed in a pouch and the electrical module left outside the sealed pouch. In other non-limiting examples, the two modules may be sealed in separate pouches.

Prior to use (e.g. just prior to use) the electrical module is combined with the reservoir module to form a single unit, which in a single action, connects the battery into the circuit and powers the device on. The terms "prior to use" and "just prior to use" are described in more detail hereinafter. In general, these terms are intended to indicate that the two parts of the device are combined by a user, and that the device is then used to deliver therapeutic agent to a patient within a predetermined window of time—e.g. from 0 to 8 hrs or from 0 to 72 hours—after the two parts of the device are combined. This predetermined window of time may vary, depending upon the therapeutic agent, the amount of agent to be delivered, requirements of various regulatory agencies, etc. For the sake of clarity, it is to be understood that combination of the electrical and reservoir modules is postponed after manufacture and is carried out at the point of use so that during shipping and storage the power source enclosed within the electrical module is electrically isolated from the circuitry until the two modules are combined by the user.

As stated before, combination of the electrical and reservoir modules connects the battery into the circuit to achieve a powered on state, without any additional action required on the part of the user. For example, there is no need for the user to activate a power switch or remove a tab in order to connect the battery into the circuit. Once the two modules have been properly combined, power is supplied to the circuitry. The circuitry can then operate normally. Normal operation may include various circuitry tests, operation of various indicators (such as the aforementioned LCD, LED and sound transducers), setting of various logic flags, detection of error states and/or logic flags, etc. Normal operation also includes reception of an activation signal, e.g. through an activation button or switch, and providing power to the electrodes through electrical outputs connected to electrical inputs on the reservoir module.

In addition to reducing corrosion and battery discharge prior to use, another advantage of the device is that the electrical outputs from the electrical module and inputs to the reservoir module (i.e. the contacts between the two modules) are electrically and physically separated from the power-on switches that connect the battery into the circuit. This is advantageous, at least because it allows the power-on switches, which connect the battery into the circuit, to be kept entirely internal to the electrical module. This in turn allows the contacts that comprise the power-on switches to be kept contaminant-free, as the electrical module is at least in some embodiments sealed against contaminants, such as water (including water vapor) and/or particulates. As described herein, a power-on switch is closed by an actuator through an elastomeric seal, which permits the battery to be connected into the circuit without the contacts that comprise the switch being exposed to the environment external to the electrical module.

In some embodiments, two or more power-on switches are employed. In some particular embodiments, the power-on switches are physically remote from one another—e.g. on the order of from 0.1 cm to several cm. In some embodiments, the switches are at least 0.5 cm from one another.

As the two modules form a unitary device, they advantageously include one or more mechanical coupler pairs to hold the two modules together. Such coupler pairs can include snap-snap receptacle pairs, which are in some embodiments designed to become inoperative (deform and/or break) if the two modules are forced apart after they are combined. Thus, devices described herein are well-suited for one time use, as they can be adapted to embody mechanical means for ensuring that the device is used only once.

In some embodiments, the device may alternatively, or additionally, employ electrical means for ensuring that the device is used only once. For example, an electrical means may employ a controller in the electrical module which increments a power-on counter when the device is powered on. In such embodiments, before or after the controller increments the counter, it detects the number of counts on the counter, and if it finds that the power-on counts exceed some predetermined value, it executes a routine to power the device off. As a non-limiting example the counter may initially be set to zero upon manufacturing. The device may then be briefly powered on by an external power supply during post-manufacturing testing, which the controller interprets as one power-on event, and thus increments the power-on counter by 1 count. Then when the device is assembled by the user prior to use, the controller interprets the connection of the battery into the circuit as a power-on event, and increments the power-on counter by 1. The controller then detects the count on the counter. If the count is 2 or less, the controller permits the device to operate normally. If however, the count is 3 or more, the controller initiates a power-off sequence.

As a second, non-limiting example, the counter may initially be set to zero upon manufacturing. The device may then be briefly powered on by an external power supply during post-manufacturing testing, which the controller interprets as one power-on event, and thus increments the power-on counter by 1 count. Then when the device is assembled by the user prior to use, the controller detects the count on the counter. If the count is 1 or less, the controller increments the power-on counter and permits the device to operate normally. If however, the count is 2 or more, the controller initiates a power-off sequence.

Although reference is made here to counting power-on sequences, other events may be counted, either in place of power-on events, in addition to power-on events, or as a proxy for power-on events. In particular, The power off sequence can be a sequence such as described in U.S. Pat. No. 6,216,003 B1, which is incorporated herein in its entirety.

In some embodiments, the device combines both mechanical (e.g. one-way snaps) and electrical (e.g. power-on counter) means to ensure that the device cannot be used more than once.

A single use may include multiple administrations of a therapeutic agent, e.g. within a particular window of time after the device has been powered on. The duration of time during which therapeutic agent may be administered and/or the number of total doses permitted to be administered by the device may be predetermined and programmed into a controller. Means for controlling the number of doses that may be administered and/or the period during which therapeutic may be administered are described e.g. in U.S. Pat. No. 6,216,003 B1, which is incorporated herein in its entirety. For the sake of clarity, the term "single use" is not intended to limit the device to a single administration of drug. Rather, the term "single use" is intended to exclude use of the device on more than one patient or on more than one occasion; it is also intended to exclude the use of an electrical module with more than one reservoir module and/or the reservoir module with more than one electrical module and/or detachment of the reservoir module from the electrical module and reattachment. Thus, single use feature is in some embodiments employed to prevent the patient or another from saving drug and using it at a later time. In some embodiments, such a feature may be employed to prevent abuse of the therapeutic agent.

In at least some embodiments of the device described herein, the device is configured to prevent contamination of the circuitry before and during use in order to reduce the likelihood of device malfunction. For example, the use environment may include emergency room, operative, post-operative or other medical treatment environments, in which potential particulate and liquid are prevalent. Accordingly, at least some embodiments of the device are configured so that one or more seals are formed in order to exclude ambient contaminants from ingress into the working parts of the device, such as in particular the circuitry. In some embodiments, one or more seals are formed around electrical contacts between the electrical outputs on the electrical module and the electrical inputs on the reservoir module.

In some embodiments, the power-on contacts are sealed from ingress of contaminants, such as particulates and fluids. In particular embodiments, the power-on contacts are sealed before the modules are combined, during the act of combination, and after the two modules are combined. In at least some such cases, the power-on contacts may be actuated (switched to a closed position) by an actuator that acts through an interposed elastomer, which maintains an impermeable seal while at the same time being deformed by an actuator (such as a post or other elongate member) to press the power-on contact into a closed position.

Other seals are possible and may be desirable. For example, a seal may be formed between the two parts (modules) when they are combined.

The device described herein may be appreciated by the person skilled in the art upon consideration of the non-limiting examples, which are depicted in the accompanying figures. Starting with FIG. 1, an exemplary electrotransport device 10 is depicted. The device comprises two parts—an upper part, referred to herein as the electrical module 20—and a lower part, referred to herein as the reservoir module 30. The electrical module 20 includes an electrical module body 200, which has a top (proximal) surface 220 and a bottom (distal) surface (not depicted in this view). The module body 200 has a rounded end 234 and a squared off end 254. The top surface 220 includes a window or aperture 204 for viewing an LCD display 208, an activation button 202 and an LED window or aperture 232. An alignment feature 206 is also visible in this view.

The reservoir module 30 includes a reservoir module body 300, which supports electrodes, reservoirs (see description herein) and input contacts 316. In this view, there can be seen upper surface 320, on which input contact seals 322, circumscribe the input contacts 316. The seals 322 form contaminant-impervious seals with corresponding members on the electrical module 20 (see description herein). The upper surface 320 of the reservoir module body 300 has a rounded end 352 and a squared off end 356. Also visible are snap receptors 310 and 312, which are configured to cooperate with corresponding snaps on the lower surface of the electrical module 20. In some embodiments, the snaps 310 and 312 are of different dimensions so that each can receive a snap of the correct dimension only, with the result that the device 10 cannot be assembled in the wrong orientation. As a visual aid to proper alignment of the two modules 20, 30, the reservoir module 30 also has an alignment feature 306, which a user can align with the alignment feature 206 on the electrical module 20 to ensure that the two modules 20, 30 are properly aligned.

Also visible in this view is a recess 314, which in some embodiments is of such a shape as to accept a complementary protruding member on the lower surface of the electrical module 20 in one orientation only. The recess 314 and the protuberance on the electrical module 20 thereby perform a keying function, further ensuring that the two modules can be assembled in one orientation only and/or guiding the user to assemble the two modules in the correct orientation. Another illustrative and non-limiting keying (alignment) feature is the asymmetry of the electrical module 20 with respect to the reservoir module 30. As depicted e.g. in FIG. 1, the rounded end 234 of the electrical module 20 corresponds to the rounded end 352 of the reservoir module; and the squared off end 254 of the electrical module 20 corresponds to the squared off end 356 of the reservoir module. The resulting asymmetry helps the user align the electrical module 20 with the reservoir module 30 and ensures that user can assemble the two modules in only one orientation. While the rounded end is depicted in this illustration as being distal to the viewer, one of skill in the art will recognize that this is but one possible orientation. As a non-limiting example, the rounded portion may be on the other end or one of the sides of the device. Additional keying features are discussed in more detail herein.

Also depicted in this view is one power-on post 318, which protrudes from the upper surface 320 of the reservoir module 30. The power-on post 318 is configured to contact a corresponding feature on the electrical module to actuate power-on switches, thereby electrically connecting the battery within the electrical module 20 into the circuitry contained therein. These features will be described in greater detail below. However, it should be noted that, while there is only one power-on post 318 depicted in this view, one of the intended power-on posts is obstructed by the perspective of the device. In some embodiments at least two posts and at least two power-on switches are considered advantageous, in that this is considered the minimum number of switches necessary to electrically isolate the battery from the rest of the circuit prior to use. However, this number is merely illustrative and any number of posts and power-on switches may be employed in the devices described herein.

Similarly, while there are two input contacts 322 depicted, and it is considered necessary that there be at least two such contacts—one positive and one negative—this number is also illustrative only; and any number of contacts—e.g. two positive and one negative, one positive and two negative, two positive and two negative—equal to or greater than two may be employed in devices according to this invention.

Figure 2:
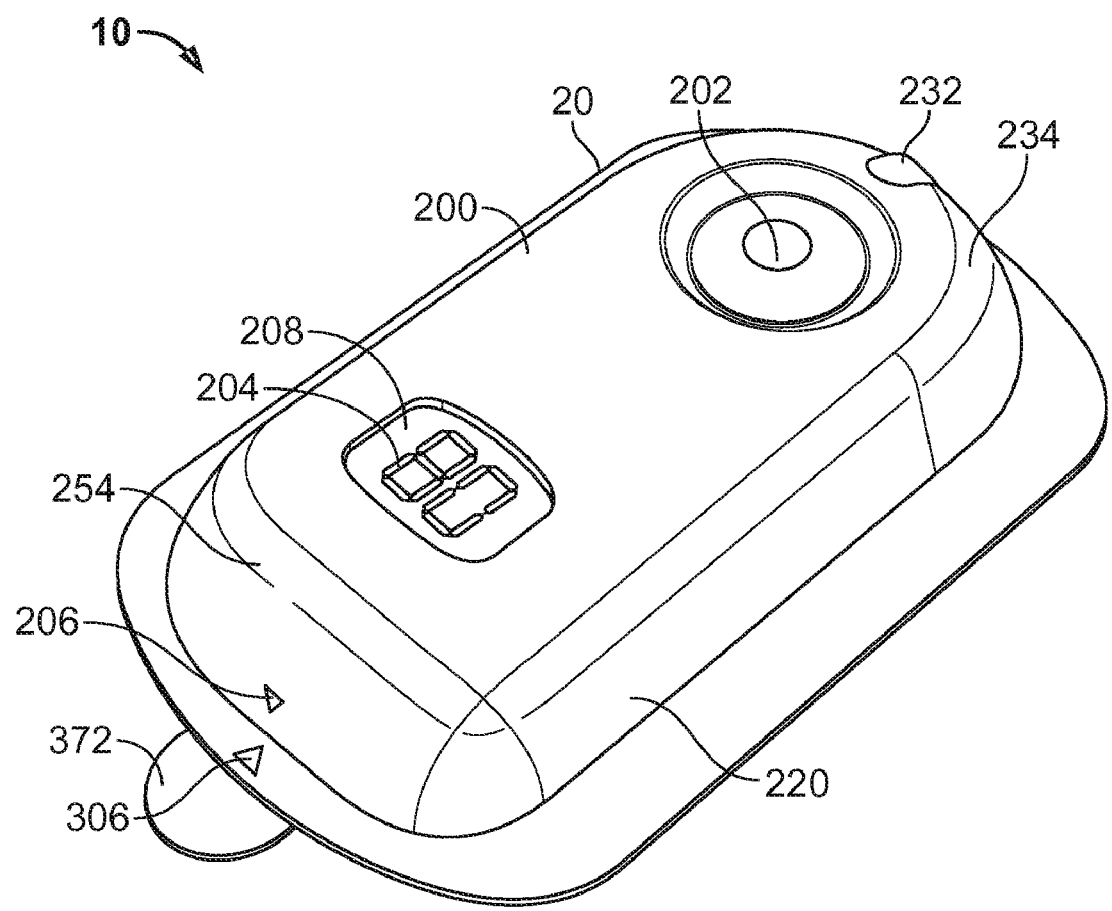
FIG. 2 shows the exemplary system of FIG. 1 combined to form a single, unitary device.

The two modules 20, 30 are combined (assembled) prior to use to form the unitary device 10 depicted in FIG. 2, in which those parts that are visible in FIG. 2 have the same numbers as used in FIG. 1.

Figure 3:
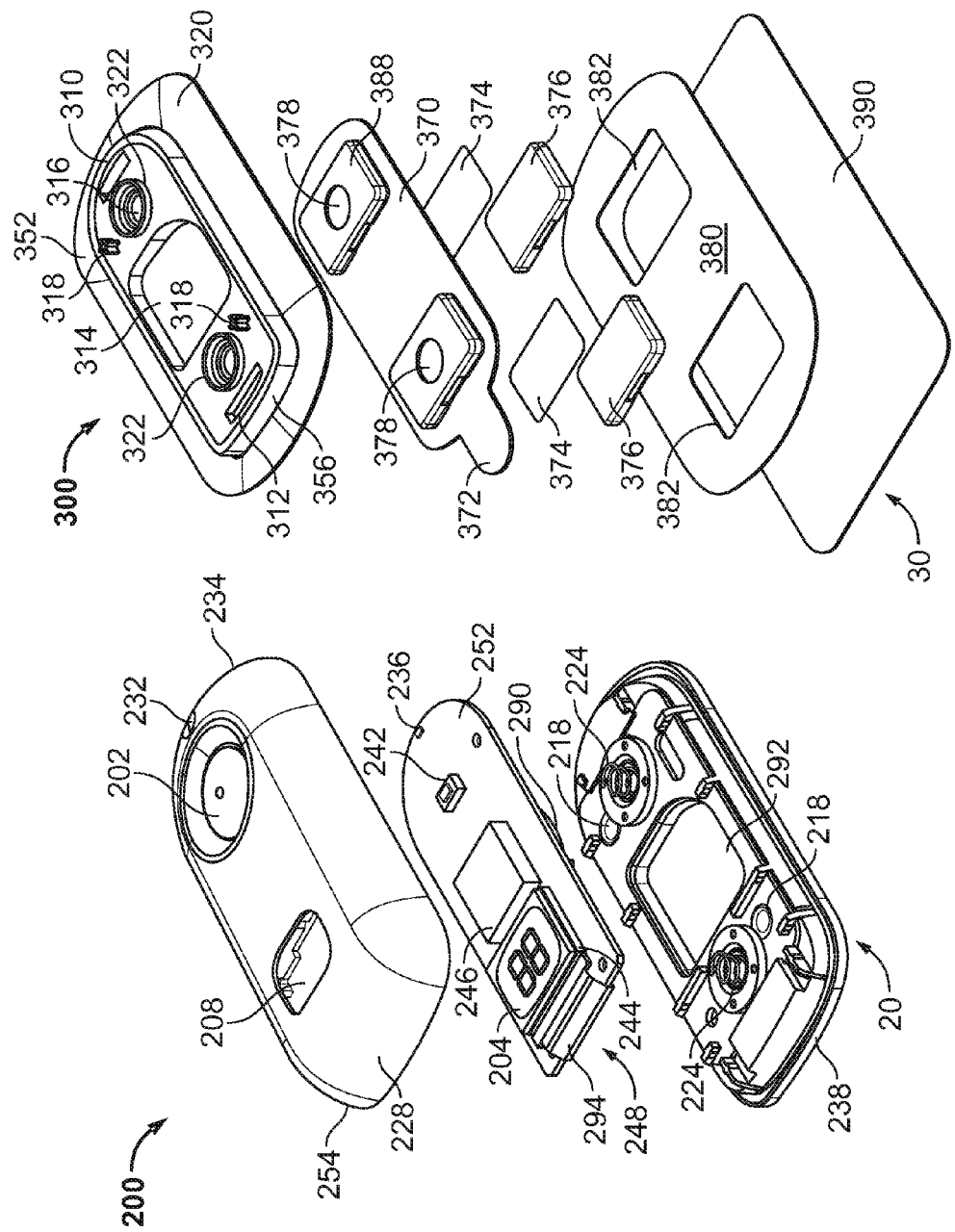
FIG. 3 shows an exploded perspective view of a two-part device.

The device 10 may be further understood by considering FIG. 3, in which the electrical module 20 and the reservoir module 30 are depicted in exploded perspective views. In the left side of FIG. 3, electrical module 20 is visible with upper electrical module body 228, lower electrical module body 238 and inner electrical module assembly 248. Visible on the upper electrical module body 228 are the activation button 202, the LED aperture or window 232, the LCD aperture or window 208. While it is also desirable in some embodiments to have an alignment feature on the upper electrical module body 228, this view does not include such an alignment feature.

Visible on the lower electrical module body 238 are the upper (proximal) surface of the elastomeric power-on receptacles 218 as well as springs 224. The function of the springs 224 will be described in more detail below. At this point it is noted that the springs 224 provide bias for connectors on the opposite side of the lower electrical module body 238.

The electrical circuit assembly 248 comprises a controller 244 beneath an LCD display 204 an LED 236 and an activation switch 242, all of which are arranged on a printed circuit board (PCB) 252. Also barely visible in this exploded view is the battery 290 on the lower side of PCB 252. The battery 290 fits within battery compartment 292 on the lower electrical module body 238. A flex circuit 294, which provides an electrical connection from the PCB 252 to the LCD display 204 is also depicted in this view. The LCD display 204 may be configured to communicate various data to a user, such as a ready indicator, a number of doses administered, a number of doses remaining, time elapsed since initiation of treatment, time remaining in the device's use cycle, battery level, error codes, etc. Likewise the LED 236 may be used to provide various data to a user, such as indicating that the power is on, the number of doses delivered, etc. The electrical circuit assembly 248 may also include a sound transducer 246 which can be configured to provide an audible "power on" signal, an audible "begin dose administration" signal, an audible error alarm, etc.

The reservoir module 30 appears in exploded perspective view in the right hand side of FIG. 3. The reservoir module 30 comprises a reservoir body 300, an electrode housing 370, an adhesive 380 and a release liner 390. The upper surface 320 of reservoir body 300 includes the recess 314, power-on posts 318, input connectors 316, seals 322 and coupler receptacles 310 and 312. The electrode housing 370 includes reservoir compartments 388. Electrode pads 374 and reservoirs 376 are inserted within the reservoir compartments 388. The electrodes 374 make contact with the input contacts 316 through the apertures 378. The adhesive 380, which provides means for attaching the device 10 to a patient, has apertures 382, through which reservoirs 376 contact the skin of a patient when the adhesive 380 is attached to a patient. The removable release liner 390 covers the reservoirs 376 and the reservoirs 376 prior to use, and is removed in order to allow the device 10 to be attached to a patient. Assembled, the electrode pads 374 contact the underside of the input connectors 316 through apertures 378, providing an electrical connection between the input connectors 316 and the reservoirs 376. Connection between the reservoirs 376 and the patient's skin is made through the apertures 382 after the release liner 390 is removed. Also visible in this view is a tab 372, which can be used to remove the electrode housing 370 from the reservoir body 300 for disposal of the reservoirs 374, which in some embodiments contain residual therapeutic agent, after the device 10 has been used.

Figure 4:
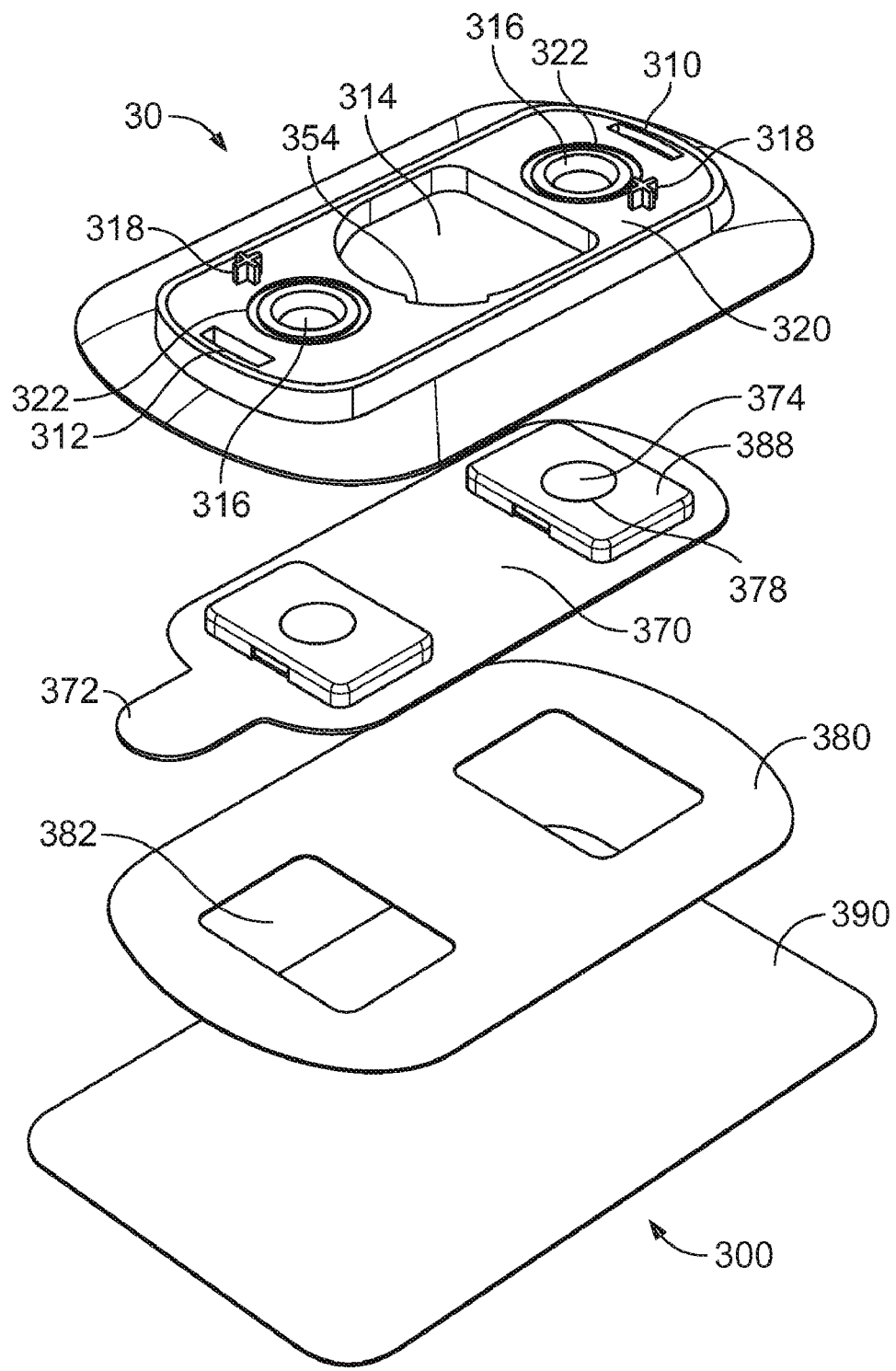
FIG. 4 shows an exploded perspective view of an exemplary reservoir module.

Another view of the reservoir module 30 appears in FIG. 4. In this view, the electrodes 374 are viewed through the apertures 378 in the reservoir compartments 388. Notable in FIG. 4 is the recess 314 has an indent 354, which is adapted to accept a complementary feature on the underside of an electrical module. This is one of many possible keying that may be provided for the device. In some embodiments, the recess 314 may receive the underside of a battery compartment in the electrical module; however the person skilled in the art will recognize that many such keying features are possible. One such keying feature may be the dimensions of the snap receptacles 310, 312 and the corresponding snaps, which permit assembly of the two modules in one configuration only. Other keying features could include the size and/or position of the electrical inputs 316 on the reservoir module 30 and the corresponding electrical outputs on the electrical module, the size and/or positions of the power-on posts 318, the complementary shapes of the reservoir module 30 and the electrical module 20.

Figure 5:
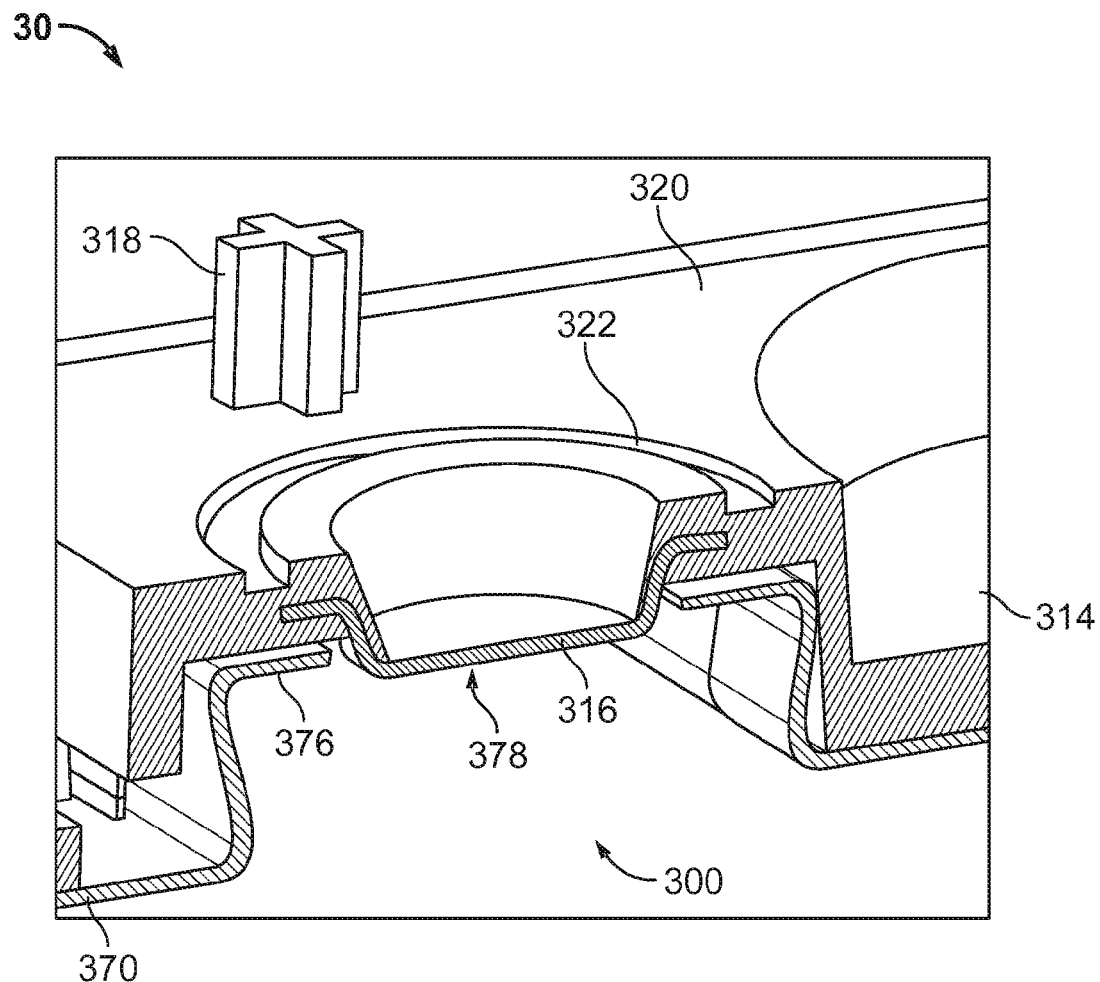
FIG. 5 is a cross-section perspective view of a reservoir contact.

FIG. 5 is a cross section perspective view of an input connector 316 on a reservoir module 30. Visible in this view are the upper surface 320 of the reservoir body 300. Circumscribing the input connector 316 is a seal 322. The seal 322 is configured to contact a corresponding seal on an electrical module to preventingress of contaminants upon assembly of the device. The contact 316 is in some embodiments advantageously a planar (flat or substantially flat) metallic contact. The contact may be essentially any conductive metal, such as copper, brass, nickel, stainless steel, gold, silver or a combination thereof. In some embodiments, the contact is gold or gold plated.

Also visible on the upper surface 320 of the reservoir module 30 is a power-on post 318 protruding from the surface 320. The lower portion of input connector 316 is configured to contact a reservoir (not pictured) through an aperture 378 in the reservoir compartment 388 in the electrode housing 370.

Additionally, part of the battery receptacle 314 may be seen in FIG. 5.

Figure 6:
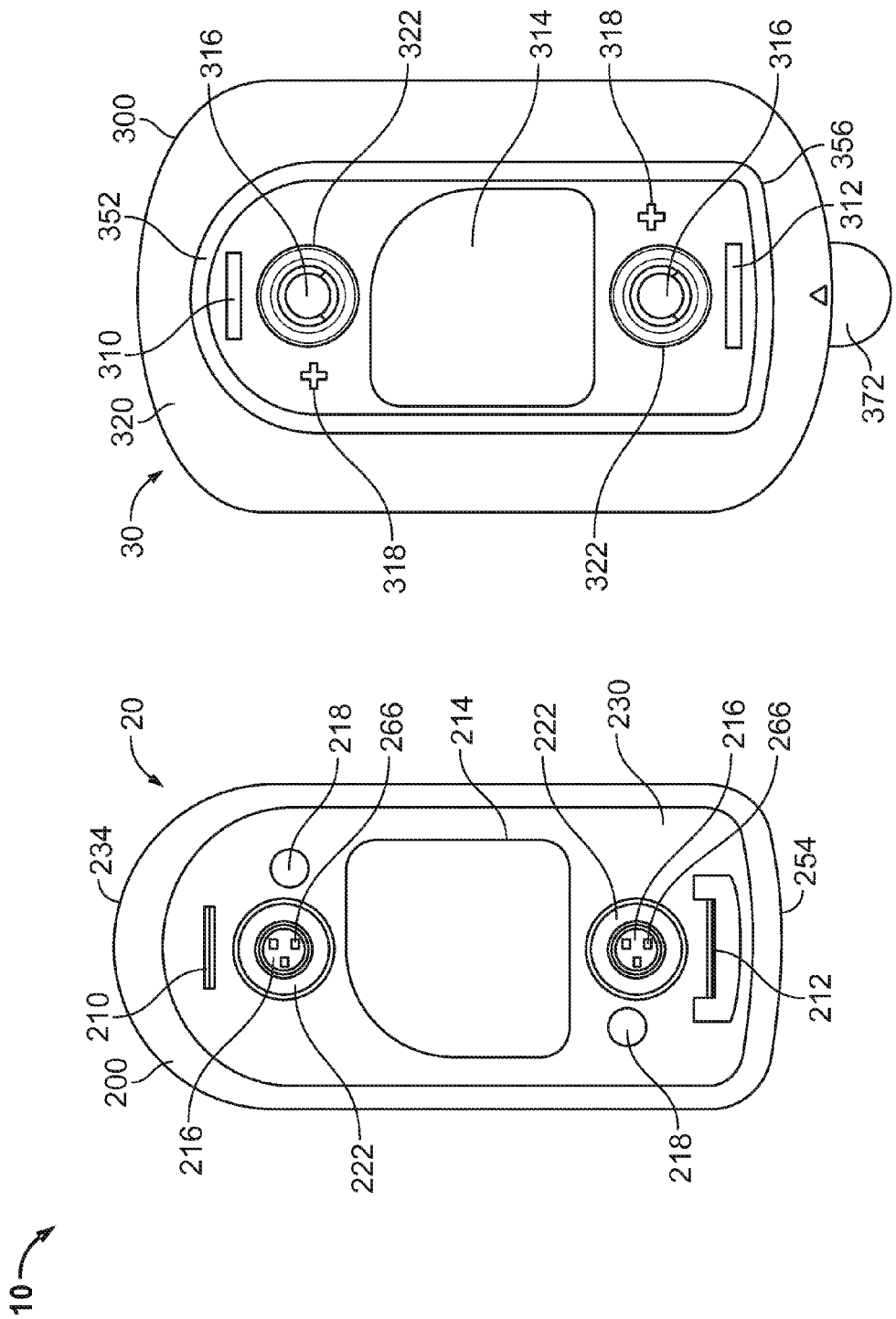
FIG. 6 shows a bottom view of an electrical module and a top view of a reservoir module.

FIG. 6 is another view of the two modules 20, 30 side by side. On the left side of FIG. 6 is the bottom side of the electrical module body 200; and on the right side is the top side of the reservoir module 30. The bottom surface 230 of electrical module body 200 has snaps 210, 212 protruding therefrom, which are sized and shaped to fit within the snap receptacles 310, 312 on the top of the reservoir module body 300. As discussed above, in some embodiments snaps 210 and 212 are of different size so that snap 210 will not fit within snap receptacle 312 and/or snap 212 will not fit within snap receptacle 310. This is one of several keying features that may be incorporated in the device 10. As an illustrative example, snap 212 cannot fit into 310, because snap 212 is larger than receptacle 310; but snap 210 can fit into receptacle 312, because it is the smaller snap an larger receptacle. In other embodiments, it is possible to size both snaps and receptacles so that the one snap/receptacle pair is larger in one dimension (e.g., horizontally), while the other snap/receptacle pair is larger in the other dimension (e.g., longitudinally). Another keying feature is the protrusion 214, which may house the battery or other component, and which is shaped to fit in one configuration within recess 314 only.

The snaps 210, 212 are at least in some embodiments one-way snaps, meaning that they are biased so as to fit within the receptacles 310, 312 in such a way that they are not easily removed, and in at least some preferred embodiments, are configured to break (or deform to the extent that they are no longer operable) if forced apart so that the modules 20, 30 cannot be reassembled to form a single unitary device. In some embodiments, such a feature is provided as an anti-abuse character to the device, such that the reservoir module 30 cannot be saved after use and employed with a different (or the same) electrical module 20.

The lower surface 230 of electrical module body 200 also has two electrical outputs 216, which are also referred to herein as output "hats", which in certain embodiments are have one or more bumps 266 protruding from the surface thereof. These hats 216 are circumscribed by hat seals 222. The hats 216 are configured to make contact with the input connectors 316 on the reservoir body 300. Additionally, the hat seals 222 are configured to contact and create an impermeable seal with the input seals 322. Advantageously the hat seals 222 are made of an elastomeric material that creates a contaminant-impermeable seal around the hats 216 and, when mated with the input connector seals 322, creates further contaminant-impermeable seals.

The power-on receptacles 218 are configured to receive input posts 318. In some embodiments, the power-on receptacles 218 are made of a deformable (e.g. elastomeric) material. In some such embodiments, the power-on posts 318 deform the power-on resceptacles 218 so that they contact power-on contacts (described in more detail below) and move them to a closed position, thereby connecting the battery into the circuit. Once the two modules 20, 30 are snapped together, the posts maintain pressure on the power-on contacts through the receptacles 218 and keep the battery in the circuit.

While the hats 216 and input contacts 316 are depicted in FIG. 6 as being essentially the same size and symmetrically disposed along the longitudinal axis of the device 10, another keying feature may be introduced into the device by changing the relative size and/or position with respect to the longitudinal axis of the hats 216 and contacts 316, the power-on posts 318 and receptacles 218, etc.

Figure 7A:
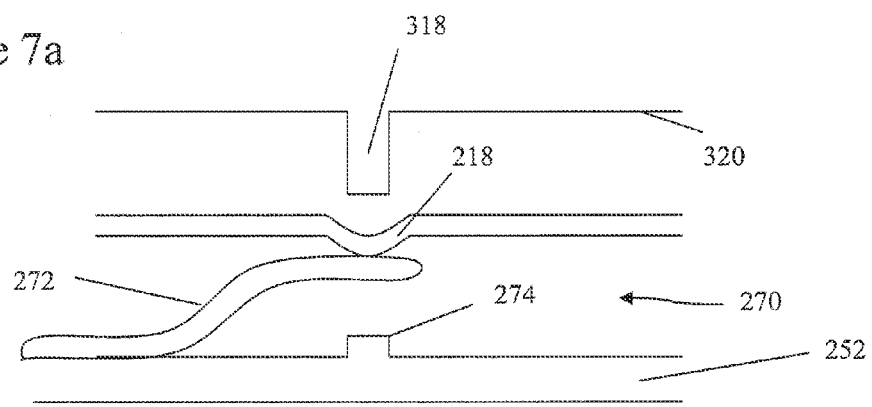
FIGS. 7a and 7b show cross-section views of a power-on connector when open (prior to actuation) and closed by a power-on post acting through a power-on receptacle.
Figure 7B:
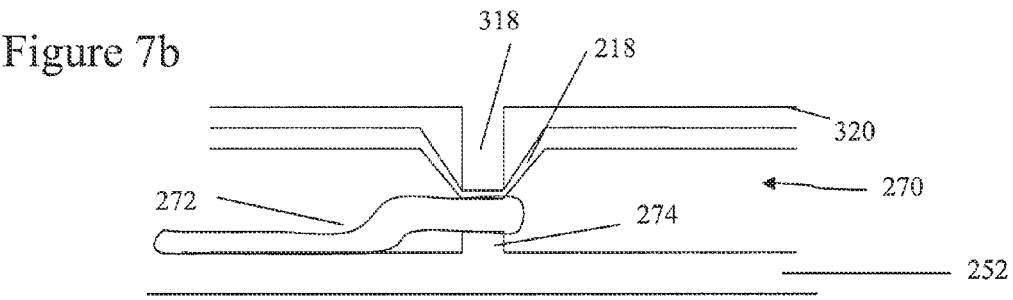

A cross section of one embodiment of a power-on switch 270 is depicted in FIGS. 7a and 7b. The power-on switch 270 comprises movable contact 272 and a stationary contact 274. Each of the movable contact 272 and the stationary contact 274 is connected to a portion of the circuitry on the printed circuit board (PCB) 252. In the open position depicted in FIG. 7a, the movable contact 272 is biased away from the stationary contact 274, whereas in the closed position depicted in FIG. 7b, the two contacts 272 and 274 are pressed together by the power-on post 318, which protrudes from the upper surface 320 of the reservoir module 30. The power-on post 318 acts through the flexible (elastomeric) power-on receptacle 218 to force the movable contact 272 down until it is in contact with the stationary contact 274. For the sake of visibility, the stationary contact 274 is shown elevated from the PCB 252; however, it will be understood that the stationary contact 274 need not be, and generally will not be, elevated from the PCB 252. In at least some embodiments, the stationary contact 274 will be an exposed metal trace on the surface of the PCB 252, though other configurations are also possible. The stationary contact 272 is manufactured from a suitably springy metal, such as a copper alloy, which is biased to remain in the first, open position unless acted on by the power-on post 318. The receptacle 218 may resemble a dome when viewed from the side of facing the contacts 272, 274, and is at least in some embodiments formed of a suitable elastomeric substance that permits the power-on post 318 to deform it without rupturing the seal. In some embodiments, the receptacle 218 may also be planar or may be domed in the opposite direction. In at least some embodiments, the receptacle 218 provides a contaminant-tight seal between the external and internal parts of the electrical module 20.

Figure 8:
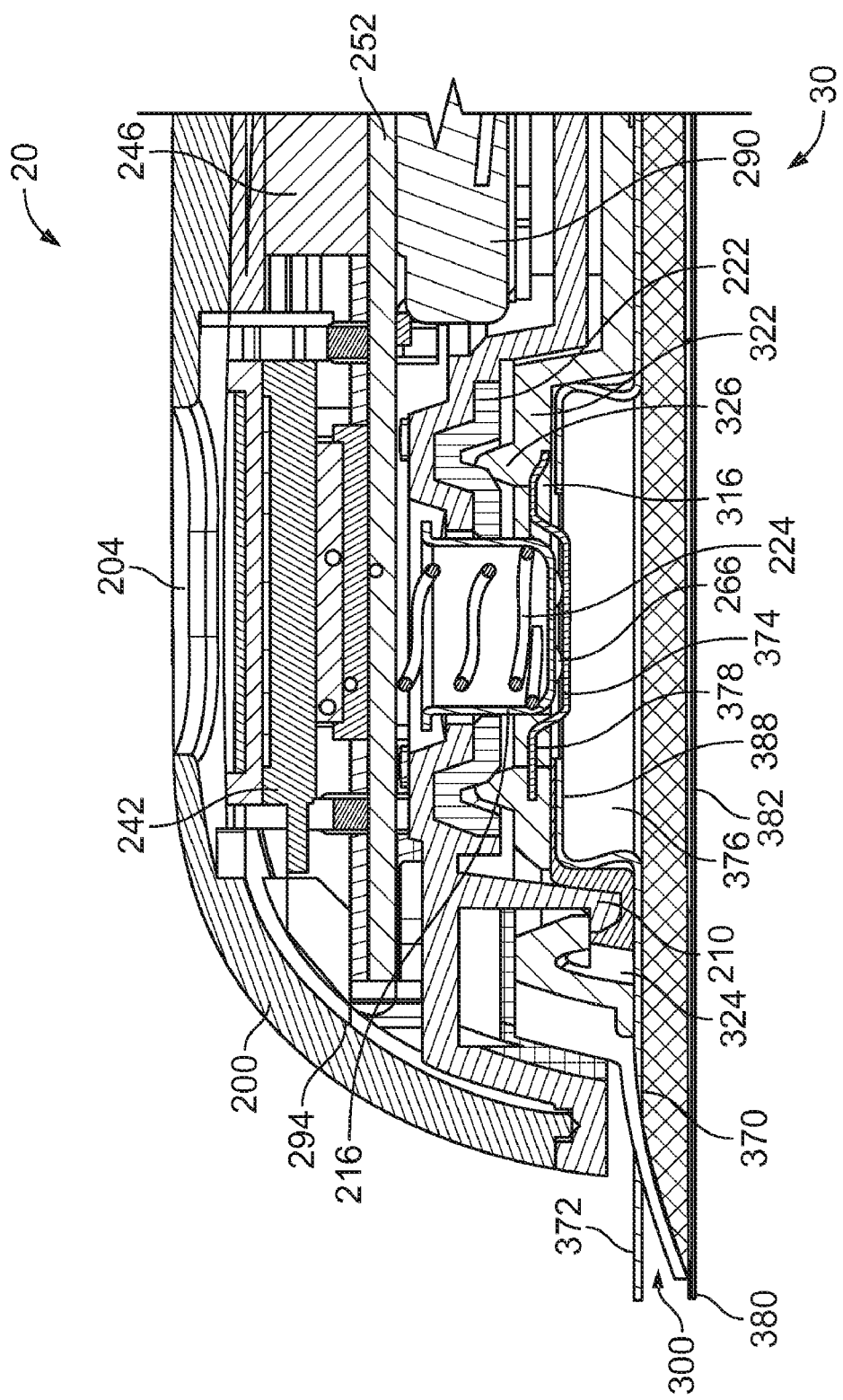
FIG. 8 shows a cross-section view of an output from the electrical module making contact with an input connector on the reservoir module.

FIG. 8 shows a cross section of a part of a device 10 in an assembled state. The device 10 comprises the upper electrical module 20, comprising an upper body 200, and the reservoir module 30, comprising reservoir body 300, which are shown in this cross section view as combined. Parts of the electrical module 20 that are visible in this cross section view include the electrical module body 200, which contains a sound transducer 246, an LCD 204, controller 242, and battery 290, all of which are on the printed circuit board (PCB) 252. A flex circuit 294 provides a connection between the PCB 252 and the LCD 204. Also visible are the contact hat 216, which has bumps 266, and snap 210. As can be seen, the contact hat 216 is biased toward the reservoir module 30 by a coil spring 224, which fits within the contact hat 216 and exerts a force through the contact hat 216 to press the contact hat 216 against the input connector 316 of the reservoir module 30. The hat 216 is circumscribed by a hat seal 222, which contacts the hat 216 through its full length of travel. In at least some embodiments, this hat seal 222 is an elastomeric seal that provides a contaminant-tight fit between the hat seal 222 and the hat 216, whereby the electrical module 20 is sealed against contaminants such as particles and fluids (e.g. humidity) in the environment.

The reservoir module 30 includes a reservoir 376 and an electrode 374 within the reservoir compartment 388 in the electrode housing 370, which also has an electrode housing tab 372. In the assembled state, the snap 210 catches on the ledge 324 of the snap receptacle 310. At least in some embodiments, the snap 210 is made of a resilient polymer and is biased to maintain contact with the ledge 324 so that the two modules 20, 30 cannot be easily separated. In some preferred embodiments, the snap 210 is configured so that if the two modules 20, 30 are separated, the snap 210 (and/or the ledge 324) will break (or deform to the extent that they are no longer operable) and thereafter be unable to couple the two modules together.

Also depicted in this view is an input connector seal 322, which in this illustration forms a ridge 326 (input connector seal ridge) that circumscribes the input connector 316. When the two modules 20, 30 are assembled, this input connector seal ridge 326 contacts and presses into the elastomeric hat seal 222, thereby preventing ingress of contaminants, such as particulates and liquids, into the space containing the output contact hat 216 and the input contact 316.

The hat 216 projects through the aperture 378 in the reservoir compartments 388. At least the bumps 266 on the hat 216 contact the input connector 316 to provide electrical contact between the electrical module 20 and the reservoir module 30. The spring 224 provides mechanical bias to force the bumps 266 to maintain contact with the input connector 316. Although the hat 216 is shown being biased by a coil spring 224, the person having skill in the art will recognize that other springs and spring-like devices can be used within the scope of the device described herein. For example, and without limitation, the coil spring 224 could be replaced by a beam spring or similar device.

Figure 9:
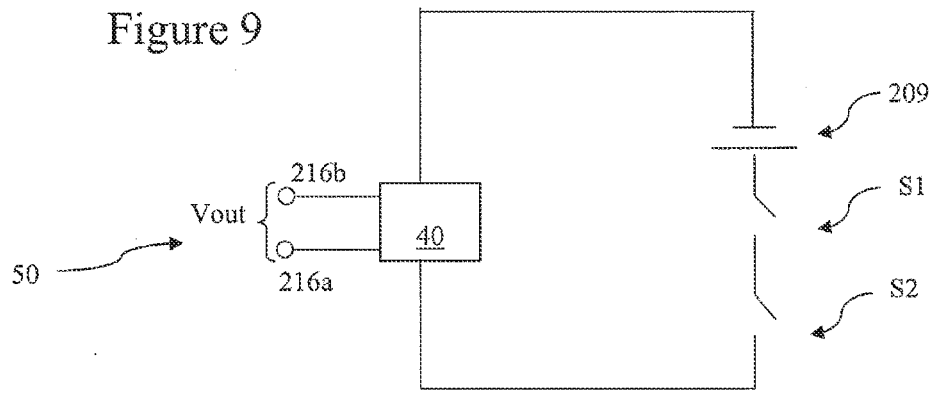
FIG. 9 is a circuit diagram for electronics within an electrical module of the device described herein.

As can be seen in FIG. 9, which is a high level schematic diagram of the electronics 50 within the electrical module 20, the electronics 50 can be envisioned as including circuitry 40 (which includes the controller, various indicators, etc.) connected to the battery 290 through power-on switches S1 and S2 (which correspond to power-on switch 270 in FIGS. 7a, 7b). The circuitry 40 controls delivery of voltage Vout through the ouputs 216a, 216b, which connect to corresponding inputs on the reservoir module. It is to be understood that, although the configuration of power-on switches S1 and S2 shown in FIGS. 7a and 7b is considered to provide certain advantages, such as ease of operation and manufacture, other configurations of switches may be employed within the scope of the device described herein. Such switches may include slides switches that are mechanically biased toward the open position, which may be pushed to the closed position by a power-on post or similar actuator. As can be seen in this figure, the circuit 50 comprising the battery 209 and the rest of the circuitry 40, is only completed if both S1 and S2 are both held closed. Prior to S1 and S2 being closed, e.g. through the mechanical action of power-on posts, the battery 290 is isolated from the circuitry 40, as the circuit is open and does not allow current to flow through it. As mentioned before, this reduces battery drain prior to use and greatly reduces corrosion, as the circuitry has no power supply, and thus no extrinsic charge, applied to it. Also, if during handling prior to use one of the switches happens to close, e.g. for a brief period of time, the device will not power on. At least in some embodiments, it is considered advantageous for the controller to detect spurious short-lived closing of both switches S1 and S2 in order to account for occasional, accidental closing of the switches before use. Also, as discussed above, it is considered advantageous in some embodiments that the two switches S1 and S2 be physically and/or electrically remote from one another. Separation of the two switches reduces the likelihood that something that causes one of the switches to malfunction (e.g. close, whether permanently, reversibly or intermittently) will not also affect the other switch. Additionally or alternatively, the two switches may be located on two different sides of the battery or on the same side of the battery. Thus, while in FIG. 9 the switches S1, S2 are depicted on the positive (+) side of the battery 290, one or both could be located on the other side of the battery. Thus, 1, 2, 3 or more switches may be located on one (positive or negative) side of the battery and 0, 1, 2, 3 or more switches may be located on the other (negative or positive) side of the battery. Physical separation of the two switches may be from 0.1 cm to several cm, and in some embodiments at least 0.5 cm.

Also apparent is FIG. 9 is that the switches S1, S2 are remote from the outputs 216a, 216b. Thus, the outputs from the electrical module to the reservoir module are separated from the switches S1, S2. Though in some preferred embodiments the closing of switches S1, S2 occurs as a result of the same action that connects the outputs 216a, 216b to the corresponding inputs on the reservoir module, the switches S1, S2 are remote from the outputs 216*a*, 216*b*. This allows switches S1, S2 to be entirely internal to the electrical module, and in some embodiments to be sealed against ingress of contaminants, such as water (including vapor) and/or particulates.

Figure 11:
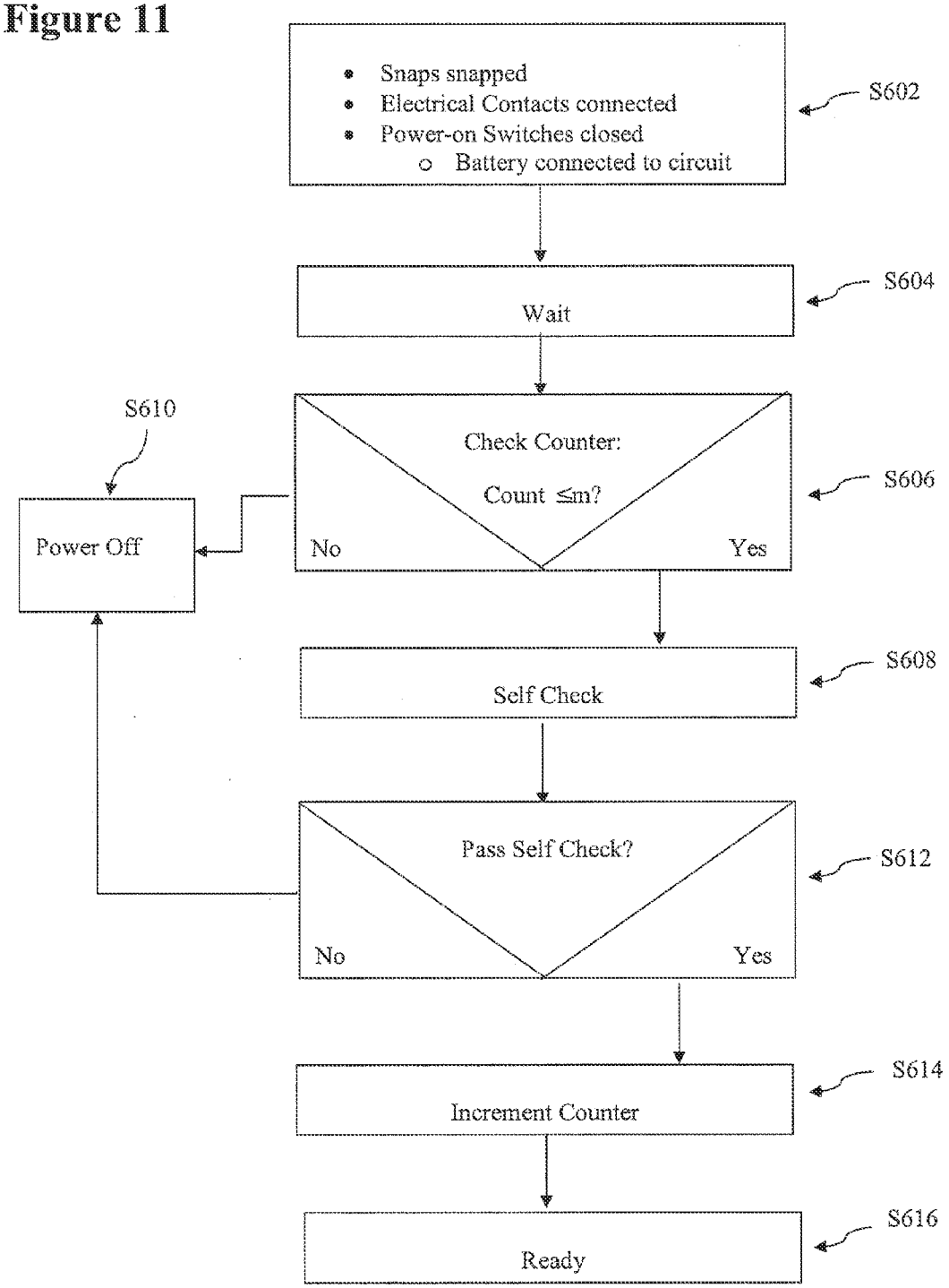
FIG. 11 is a second flow chart showing an alternative power-on sequence of a device as described herein.

FIGS. 10 and 11 provide two alternative power-on sequences for a device 10 according as described herein. The first alternative in FIG. 20 shows that in the first step, S502, four events occur all at once in a single action by the user: the snaps are snapped into their respective receptacles; the output and input contacts are mated to provide electrical contact between the reservoirs in the reservoir module and the circuitry in the electrical module; the power-on posts close the power-on switches in the electrical module; and the battery is thereby connected into the circuit and begins providing power to the circuitry. In step S504 the controller waits a minimum period of time (e.g. 10-500 ms) before proceeding to the next step. In some embodiments, S504 is eliminated from the power-on sequence. In embodiments in which S504 is included in the power-on sequence, if the controller fails to maintain power for a predetermined minimum period of time, that is, e.g. power is lost during this timeframe, the timer resets to zero. Presuming that power is maintained through the time period of step S504, the controller then increments the power-on counter by 1 in step S506. In step S508, the controller then checks the number of counts on the power-on counter, and if it is less than or equal to a certain predetermined number (in this example 2, presuming that the counter had been set to 1 by an in-factory test, though other values are possible) the controller proceeds to step S510, which includes a self check. If, however, the count is greater than the predetermined number, then the controller initiates step S516, which includes a power off sequence, which may include sending an error message to an LCD display, activating an LED indicator and/or sounding an audible alarm. If the count is less than or equal to the predetermined number, the controller initiates step S510. After the self check of S510 is completed, the controller determines whether the circuitry has passed the self check, and if not, it initiates step S516. If the circuitry passes the self test check, the controller then initiates S512, which may include signaling the user that the device is ready (e.g. through the LCD, LED and/or sound transducer). The device is then ready to be applied to the body of a patient and operated normally, e.g. as described in U.S. Pat. No. 6,216,033 B1, which is incorporated herein by reference in its entirety.

A second alternative in FIG. 11 shows that in the first step, S602, four events occur all at once in a single action by the user: the snaps are snapped into their respective receptacles; the output and input contacts are mated to provide electrical contact between the reservoirs in the reservoir module and the circuitry in the electrical module; the power-on posts close the power-on switches in the electrical module; and the battery 290 is thereby connected into the circuit and begins providing potential to the circuitry. In step S604 the controller waits a minimum period of time (e.g. 10-500 ms) before proceeding to the next step. If the controller fails to maintain power for this period of time, that is, power is lost during this timeframe, the timer resets to zero. Presuming that power is maintained through the time period of step S604, the controller then checks the number of counts on the power-on counter in S606, and if it is less than or equal to a certain predetermined number (in this example 1, presuming that the counter had been set to 1 by an in-factory test, though other values are possible) the controller proceeds to step S610, which includes a self check. If, however, the count is greater than the predetermined number, then the controller initiates step S616, which includes a power off sequence, which may include sending an error message to an LCD display, activating an LED indicator and/or sounding an audible alarm. If the count is less than or equal to the predetermined number, the controller initiates step S610. After the self check of S610 is completed, the controller determines whether the circuitry has passed the self check, and if not, it initiates step S616. If the circuitry passes the self test check, the controller then initiates S612, which includes incrementing the counter by 1. The controller then initiates S614, which may include signaling the user that the device is ready (e.g. through the LCD, LED and/or sound transducer). The device is then ready to be applied to the body of a patient and operated normally, e.g. as described in U.S. Pat. No. 6,216,033 B1, which is incorporated herein by reference in its entirety.

Briefly described, the device is applied to the surface of a patient's skin. The patient or a healthcare professional may then press the button 202 (see FIGS. 1, 2, 3). In some embodiments, the device is configured to require the patient or healthcare professional to press the button twice within a predetermined timeframe in order to prevent accidental or spurious administration of the therapeutic agent. Provided the patient or healthcare professional properly presses the button 202, the device 10 then begins administering the therapeutic agent to the patient. Once a predetermined number of doses has been administered and/or a predetermined period of time has elapsed since the device was powered on, the device initiates a power off sequence, which may include sending a power off signal to the user through an LCD display, an LED and/or an audio transducer. See especially the claims of U.S. Pat. No. 6,216,033 B1, which are incorporated herein by reference.

The person skilled in the art will recognize that other alternative power-on sequences may be employed. For example, the controller may increment the counter immediately after the counter check in the process outlined in FIG. 10 or 11.

The reservoir of the electrotransport delivery devices generally contain a gel matrix, with the drug solution uniformly dispersed in at least one of the reservoirs. Other types of reservoirs such as membrane confined reservoirs are possible and contemplated. The application of the present invention is not limited by the type of reservoir used. Gel reservoirs are described, e.g., in U.S. Pat. Nos. 6,039,977 and 6,181,963, which are incorporated by reference herein in their entireties. Suitable polymers for the gel matrix can comprise essentially any synthetic and/or naturally occurring polymeric materials suitable for making gels. A polar nature is preferred when the active agent is polar and/or capable of ionization, so as to enhance agent solubility. Optionally, the gel matrix can be water swellable nonionic material.

Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly(allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

Incorporation of the drug solution into the gel matrix in a reservoir can be done in any number of ways, i.e., by imbibing the solution into the reservoir matrix, by admixing the drug solution with the matrix material prior to hydrogel formation, or the like. In additional embodiments, the drug reservoir may optionally contain additional components, such as additives, permeation enhancers, stabilizers, dyes, diluents, plasticizer, tackifying agent, pigments, carriers, inert fillers, antioxidants, excipients, gelling agents, anti-irritants, vasoconstrictors and other materials as are generally known to the transdermal art. Such materials can be included by on skilled in the art.

The drug reservoir can be formed of any material as known in the prior art suitable for making drug reservoirs. The reservoir formulation for transdermally delivering cationic drugs by electrotransport is preferably composed of an aqueous solution of a water-soluble salt, such as HCl or citrate salts of a cationic drug, such as fentanyl or sufentanil. More preferably, the aqueous solution is contained within a hydrophilic polymer matrix such as a hydrogel matrix. The drug salt is preferably present in an amount sufficient to deliver an effective dose by electrotransport over a delivery period of up to about 20 minutes, to achieve a systemic effect. The drug salt typically includes about 0.05 to 20 wt % of the donor reservoir formulation (including the weight of the polymeric matrix) on a fully hydrated basis, and more preferably about 0.1 to 10 wt % of the donor reservoir formulation on a fully hydrated basis. In one embodiment the drug reservoir formulation includes at least 30 wt % water during transdermal delivery of the drug. Delivery of fentanyl and sufentanil has been described in U.S. Pat. No. 6,171,294, which is incorporated by reference herein. The parameter such as concentration, rate, current, etc. as described in U.S. Pat. No. 6,171,294 can be similarly employed here, since the electronics and reservoirs of the present invention can be made to be substantially similar to those in U.S. Pat. No. 6,171,294.

The drug reservoir containing hydrogel can suitably be made of any number of materials but preferably is composed of a hydrophilic polymeric material, preferably one that is polar in nature so as to enhance the drug stability. Suitable polar polymers for the hydrogel matrix include a variety of synthetic and naturally occurring polymeric materials. A preferred hydrogel formulation contains a suitable hydrophilic polymer, a buffer, a humectant, a thickener, water and a water soluble drug salt (e.g. HCl salt of an cationic drug). A preferred hydrophilic polymer matrix is polyvinyl alcohol such as a washed and fully hydrolyzed polyvinyl alcohol (PVOH), e.g. MOWIOL 66-100 commercially available from Hoechst Aktiengesellschaft. A suitable buffer is an ion exchange resin which is a copolymer of methacrylic acid and divinylbenzene in both an acid and salt form. One example of such a buffer is a mixture of POLACRILIN (the copolymer of methacrylic acid and divinyl benzene available from Rohm & Haas, Philadelphia, Pa.) and the potassium salt thereof. A mixture of the acid and potassium salt forms of POLACRLIN functions as a polymeric buffer to adjust the pH of the hydrogel to about pH 6. Use of a humectant in the hydrogel formulation is beneficial to inhibit the loss of moisture from the hydrogel. An example of a suitable humectant is guar gum. Thickeners are also beneficial in a hydrogel formulation. For example, a polyvinyl alcohol thickener such as hydroxypropyl methylcellulose (e.g. METHOCEL K100 MP available from Dow Chemical, Midland, Mich.) aids in modifying the rheology of a hot polymer solution as it is dispensed into a mold or cavity. The hydroxypropyl methylcellulose increases in viscosity on cooling and significantly reduces the propensity of a cooled polymer solution to overfill the mold or cavity.

Polyvinyl alcohol hydrogels can be prepared, for example, as described in U.S. Pat. No. 6,039,977. The weight percentage of the polyvinyl alcohol used to prepare gel matrices for the reservoirs of the electrotransport delivery devices, in certain embodiments can be about 10% to about 30%, preferably about 15% to about 25%, and more preferably about 19%. Preferably, for ease of processing and application, the gel matrix has a viscosity of from about 1,000 to about 200,000 poise, preferably from about 5,000 to about 50,000 poise. In certain preferred embodiments, the drug-containing hydrogel formulation includes about 10 to 15 wt % polyvinyl alcohol, 0.1 to 0.4 wt % resin buffer, and about 1 to 30 wt %, preferably 1 to 2 wt % drug. The remainder is water and ingredients such as humectants, thickeners, etc. The polyvinyl alcohol (PVOH)-based hydrogel formulation is prepared by mixing all materials, including the drug, in a single vessel at elevated temperatures of about 90 degree C. to 95 degree C. for at least about 0.5 hour. The hot mix is then poured into foam molds and stored at freezing temperature of about −35 degree C. overnight to cross-link the PVOH. Upon warming to ambient temperature, a tough elastomeric gel is obtained suitable for ionic drug electrotransport.

A variety of drugs can be delivered by electrotransport devices. In certain embodiments, the drug is a narcotic analgesic agent and is preferably selected from the group consisting of fentanyl and related molecules such as remifentanil, sufentanil, alfentanil, lofentanil, carfentanil, trefentanil as well as simple fentanyl derivatives such as alpha-methyl fentanyl, 3-methyl fentanyl and 4-methyl fentanyl, and other compounds presenting narcotic analgesic activity such as alphaprodine, anileridine, benzylmorphine, beta-promedol, bezitramide, buprenorphine, butorphanol, clonitazene, codeine, desomorphine, dextromoramide, dezocine, diampromide, dihydrocodeine, dihydrocodeinone enol acetate, dihydromorphine, dimenoxadol, dimeheptanol, dimethylthiambutene, dioxaphetyl butyrate, dipipanone, eptazocine, ethylmethylthiambutene, ethylmorphine, etonitazene, etorphine, hydrocodone, hydromorphone, hydroxypethidine, isomethadone, ketobemidone, levorphanol, meperidine, meptazinol, metazocine, methadone, methadyl acetate, metopon, morphine, heroin, myrophine, nalbuphine, nicomorphine, norlevorphanol, normorphine, norpipanone, oxycodone, oxymorphone, pentazocine, phenadoxone, phenazocine, phenoperidine, piminodine, piritramide, proheptazine, promedol, properidine, propiram, propoxyphene, and tilidine.

Some ionic drugs are polypeptides, proteins, hormones, or derivatives, analogs, mimics thereof. For example, insulin or mimics are ionic drugs that can be driven by electrical force in electrotransport.

For more effective delivery by electrotransport salts of certain pharmaceutical analgesic agents are preferably included in the drug reservoir. Suitable salts of cationic drugs, such as narcotic analgesic agents, include, without limitation, acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, .beta.-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate. The more preferred salt is chloride.

A counterion is present in the drug reservoir in amounts necessary to neutralize the positive charge present on the cationic drug, e.g. narcotic analgesic agent, at the pH of the formulation. Excess of counterion (as the free acid or as a salt) can be added to the reservoir in order to control pH and to provide adequate buffering capacity. In one embodiment of the invention, the drug reservoir includes at least one buffer for controlling the pH in the drug reservoir. Suitable buffering systems are known in the art.

The device described herein is also applicable where the drug is an anionic drug. In this case, the drug is held in the cathodic reservoir (the negative pole) and the anoidic reservoir would hold the counterion. A number of drugs are anionic, such as cromolyn (antiasthmatic), indomethacin (anti-inflammatory), ketoprofen (anti-inflammatory) and ketorolac tromethamine (NSAID and analgesic activity), and certain biologics such as certain protein or polypeptides.

Method of Making

A device according to the present invention can be made by forming the layers separately and assembling the layers into the electronic module and the reservoir module. The polymeric layers can be made by molding. Some of the layers can be applied together and secured. Some of the layers can be comolded, for example, by molding a second layer onto a first layer. For example, the upper layer and lower layer of the upper cover (or top cover) can be comolded together. Some of the layers can be affixed together by adhesive bonding or mechanical anchoring. Such chemical adhesive bonding methods and mechanical anchoring methods are known in the art. As described before, once the electronic module and the reservoir module are formed, they can be packaged separately. Before use, the two modules can be removed from their respective packages and assembled to form the device for electrotransport. The device can then be applied to the body surface by adhesion.

The above-described exemplary embodiments are intended to be illustrative in all respects, rather than restrictive, of the present invention. Thus the present invention is capable of many variations in detailed implementation that can be derived from the description contained herein by a person skilled in the art, e.g., by permutation or combination of various features. Although iontophoretic devices are described in detail as illustration for showing how an electronic module and an agent module are coupled and work together, a person skilled in the art will know that electronic module and agent module in other electrotransport devices can be similarly coupled and work together. All such variations and modifications are considered to be within the scope of the present invention. The entire disclosure of each patent, patent application, and publication cited or described in this document is hereby incorporated herein by reference.

While preferred embodiments of the present invention have been shown and described herein, those skilled in the art will recognize that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A corrosion-resistant electrotransport drug delivery device comprising an electrical module and a reservoir module, the electrical module and the reservoir module configured to be combined to form a unitary, activated drug delivery device prior to use, wherein the device resists corrosion by electrically isolating a circuitry in the electrical module from a power source,
further wherein the electrical module comprises:
the circuitry;
an electrical output adapted to connect the circuitry to an input connector on the reservoir module when the electrical module is combined with the reservoir module; and
at least two power-on contacts between the circuitry and a battery;
wherein the battery is isolated from the circuitry by the power-on contacts while at least one of the power-on contacts remain open, and the battery is connected into the circuitry when all of the power-on contacts are closed by battery contact actuators on the reservoir module when the electrical module and the reservoir module are combined; and
wherein the reservoir module comprises:
an electrical input adapted to electrically connect the circuitry in the electrical module to at least a pair of active electrodes in the reservoir module when the electrical module is combined with the reservoir module; and
at least two battery contact actuators each configured to close a corresponding power-on contact when the electrical module is combined with the reservoir module so that the battery is connected into the circuitry and the device is powered on, wherein at least two battery contact actuators are separated from each other.

2. The device of claim 1, wherein a seal is formed upon combining the electrical module and the reservoir module.

3. The device of claim 1, further comprising a seal sealing each power-on contact before the modules are combined, each seal being configured to maintain the sealing when the power-on contact is closed by the battery contact actuator, wherein the seal is water- and/or particulate-tight.

4. The device of claim 3, wherein each seal is a flexible polymer cover over the power-on contact, which is configured to be deformed by the battery contact actuator when the electrical module is combined with the reservoir module, whereby the battery contact actuator mechanically acts through the seal to close the power-on contact.

5. The device of claim 1, further comprising a seal sealing the electrical output before, during, and after the electrical module is combined with the reservoir module.

6. The device of claim 2, wherein the seal is water- and/or particulate-tight.

7. The device of claim 1, wherein the electrical output is configured to flex while continuously applying a force on the electrical input of the reservoir module to ensure good electrical connection between the two.

8. The device of claim 7, wherein at least one surface of the electrical input is substantially planar.

9. The device of claim 1, further comprising a coupler on the reservoir module or the electrical module which couples with a corresponding coupler receptor on the electrical module or reservoir module, respectively, to prevent the unitary activated drug delivery device from being separated.

10. The device of claim 9, wherein the coupler is a snap mechanically biased to snap into a corresponding snap receptor.

11. The device of claim 10, wherein the snap is a one-way snap.

12. The device of claim 9, comprising two couplers and two corresponding coupler receptors.

13. The device of claim 12, wherein the couplers are of different sizes, whereby each coupler can be inserted only into its correspondingly sized coupler receptor, thereby ensuring that the device can be assembled in only one configuration.

14. The device of claim 9, wherein the coupler is biased so that once the coupler is engaged with its corresponding receptor, the device cannot be disassembled without breaking the coupler.

15. The device of claim 9, wherein a water- and/or particulate-tight seal is formed between the coupler and the coupler receptor when they are coupled.

16. The device of one of claim 1, wherein the battery contact actuators protrude from the reservoir module and are each adapted to depress a receptacle on the electrical module when the electrical module is combined with the reservoir module, the receptacles being in mechanical communication with the power-on contacts such that the battery is connected into the circuit when the battery contact actuators depresses the receptacle.

17. The device of claim 16, wherein at least one receptacle is a deformable member.

18. The device of claim 17, wherein the deformable member is indented, flush or domed.

19. The device of claim 1, wherein the battery is housed in a compartment that protrudes from the electrical module, which compartment has an outer shape that is configured to a corresponding indentation in the reservoir module such that the battery compartment fits snugly within the indentation in only one configuration when the electrical module and the reservoir module are combined to form the unitary device.

20. The device of claim 1, further comprising a sealing member adapted to provide a seal around the electrical input and electrical output when the electrical module and the reservoir module are combined to form the unitary device.

21. The device of claim 1, wherein the electrical module further comprises a controller.

22. The device of claim 21, wherein the controller is configured to execute a power-on check when the battery is connected into the circuitry.

23. The device of claim 1, wherein the device is configured to increment a logic flag when the electrical module is combined with the reservoir module, and wherein the device is configured such that, if the logic flag has met or exceeded a predetermined value, the device will either not power on or will power off if it has already powered on.

24. The device of claim 23, wherein the device is configured to record an error code if the logic flag has met or exceeded a predetermined value.

25. The device of claim 1, wherein the power-on contact is configured to remove the battery from the circuitry if the electrical module and the reservoir module are separated after they have been combined.

26. The device of claim 2, wherein the electrical module is configured to flex while maintaining the seal.

27. The device of claim 1, wherein the battery contact actuators are separated from each other by at least 0.5 cm.

28. A corrosion-resistant electrotransport drug delivery device comprising an electrical module and a reservoir module, the electrical module and the reservoir module configured to be combined to form a unitary, activated drug delivery device prior to use,
wherein the electrical module comprises:
circuitry;
a power-on counter comprising a logic flag configured to increment when the circuitry is powered on;
an electrical output adapted to connect the circuitry to an input connector on the reservoir module when the electrical module is combined with the reservoir module;
wherein the battery is isolated from the circuitry until the electrical module and the reservoir module are combined; and
wherein the reservoir module comprises:
an electrical input adapted to electrically connect the circuitry in the electrical module to at least a pair of active electrodes in the reservoir module when the electrical module is combined with the reservoir module;
wherein the circuitry powers the device off, or will not power the device on, if the number of counts in the power-on counter exceeds a predetermined value.

29. A corrosion-resistant electrotransport drug delivery device comprising an electrical module and a reservoir module, the electrical module and the reservoir module configured to be combined to form a unitary, activated drug delivery device prior to use, wherein the device resists corrosion by electrically isolating a circuitry in the electrical module from a power source,
further wherein the electrical module comprises:
the circuitry;
an electrical output adapted to connect the circuitry to an input connector on the reservoir module when the electrical module is combined with the reservoir module; and
one or more power-on contacts between the circuitry and a battery;
a first seal sealing the one or more power-on contacts before the modules are combined, the first seal being configured to maintain the sealing when the power-on contact is closed by an actuator, wherein the first seal is water- and/or particulate-tight;
a second seal sealing the electrical output before, during and after the electrical module is combined with the reservoir module;
wherein the battery is isolated from the circuitry by the one or more power-on contacts while the one or more power-on contacts remain open, and wherein the battery is connected into the circuitry when the one or more power-on contacts is closed by one or more battery contact actuators on the reservoir module when the electrical module and the reservoir module are combined; and
the reservoir module comprises:
an electrical input adapted to electrically connect the circuitry in the electrical module to at least a pair of active electrodes in the reservoir module when the electrical module is combined with the reservoir module; and
the one or more battery contact actuators configured to close a corresponding power-on contact when the electrical module is combined with the reservoir module, such that the battery is connected into the circuitry and the device is powered on.

* * * * *

UNITED STATES PATENT AND TRADEMARK OFFICE
CERTIFICATE OF CORRECTION

PATENT NO. : 8,301,238 B2  
APPLICATION NO. : 13/250031  
DATED : October 30, 2012  
INVENTOR(S) : Netzel et al.

Page 1 of 1

It is certified that error appears in the above-identified patent and that said Letters Patent is hereby corrected as shown below:

Claim 16, column 23, line 13; after "The device" and before "of claim 1" delete "of one".

Signed and Sealed this  
Nineteenth Day of February, 2013

Teresa Stanek Rea  
*Acting Director of the United States Patent and Trademark Office*